(12) United States Patent
Zhang et al.

(10) Patent No.: US 11,911,498 B2
(45) Date of Patent: *Feb. 27, 2024

(54) LOW pH SKIN CARE COMPOSITION AND METHODS OF USING THE SAME

(71) Applicant: The Procter & Gamble Company, Cincinnati, OH (US)

(72) Inventors: Lu Zhang, Singapore (SG); Sudeep Chakravarty, Singapore (SG); Joseph Michael Zukowski, Blue Ash, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 130 days.

This patent is subject to a terminal disclaimer.

(21) Appl. No.: 17/215,988

(22) Filed: Mar. 29, 2021

(65) Prior Publication Data

US 2021/0369587 A1 Dec. 2, 2021

Related U.S. Application Data

(63) Continuation of application No. 16/891,491, filed on Jun. 3, 2020, now Pat. No. 10,959,933.

(Continued)

(51) Int. Cl.
*A61K 8/67* (2006.01)
*A61K 8/06* (2006.01)
(Continued)

(52) U.S. Cl.
CPC ............... *A61K 8/675* (2013.01); *A61K 8/06* (2013.01); *A61K 8/365* (2013.01); *A61K 8/8147* (2013.01);
(Continued)

(58) Field of Classification Search
None
See application file for complete search history.

(56) References Cited

U.S. PATENT DOCUMENTS 3,755,560 A 8/1973 Dickert et al.
3,856,941 A 12/1974 Turner
(Continued)

FOREIGN PATENT DOCUMENTS

AU 2005293830 B2 10/2010
AU 2016206278 A1 2/2017
(Continued)

OTHER PUBLICATIONS

Bissett et al., "Topical niacinamide reduces yellowing, wrinkling, red blotchiness, and hyperpigmented spots in aging facial skin", International Journal of Cosmetic Science, 2004, vol. 26, pp. 231-238.
(Continued)

*Primary Examiner* — Bethany P Barham
*Assistant Examiner* — Barbara S Frazier
(74) *Attorney, Agent, or Firm* — Alexandra S. Anoff (57) ABSTRACT

Disclosed is an efficacious, low-pH skin care composition that provides good sensory properties and has a low skin irritation potential. The low-pH composition includes an effective amount of a vitamin $B_3$ compound and, optionally, one or more additional skin care actives to provide a skin health and/or appearance benefit. The low-pH composition also includes a pH buffer comprising lactic acid and sodium lactate, a polymer thickener comprising polyacrylate crosspolymer-6, and a silicone fluid having a kinematic viscosity of 100 cSt or less at 25° C. The pH of the low-pH composition can range from 2.0 to 5.0.

19 Claims, 1 Drawing Sheet

Related U.S. Application Data (60) Provisional application No. 63/032,992, filed on Jun. 1, 2020.

(51) Int. Cl.

| | | |
|---|---|---|
| *A61K 8/365* | (2006.01) | |
| *A61K 8/81* | (2006.01) | |
| *A61K 8/891* | (2006.01) | |
| *A61Q 17/04* | (2006.01) | |
| *A61Q 19/00* | (2006.01) | |
| *A61Q 19/02* | (2006.01) | |
| *A61Q 19/08* | (2006.01) | |
| *A61Q 19/10* | (2006.01) | |

(52) U.S. Cl.
CPC .............. *A61K 8/891* (2013.01); *A61Q 17/04* (2013.01); *A61Q 19/00* (2013.01); *A61Q 19/005* (2013.01); *A61Q 19/007* (2013.01); *A61Q 19/02* (2013.01); *A61K 2800/28* (2013.01); *A61K 2800/48* (2013.01); *A61Q 19/008* (2013.01); *A61Q 19/08* (2013.01); *A61Q 19/10* (2013.01)

(56) References Cited

U.S. PATENT DOCUMENTS

| | | |
|---|---|---|
| 3,859,436 A | 1/1975 | Jacobi |
| 3,867,549 A | 2/1975 | Costello |
| 3,892,853 A | 7/1975 | Cobble |
| 4,007,266 A | 2/1977 | Choay |
| 4,067,975 A | 1/1978 | Yu et al. |
| 4,178,372 A | 12/1979 | Coats |
| 4,406,884 A | 9/1983 | Fawzi |
| 4,421,769 A | 12/1983 | Dixon et al. |
| 4,481,187 A | 11/1984 | Kondo |
| 4,485,091 A | 11/1984 | Fitton |
| 4,792,443 A | 12/1988 | Filomeno |
| 4,879,107 A | 11/1989 | Vanlerberghe |
| 4,923,977 A | 5/1990 | Lang |
| 4,981,845 A | 1/1991 | Pereira |
| 4,981,948 A | 1/1991 | Kawachi et al. |
| 5,053,230 A | 10/1991 | Gazzani |
| 5,140,043 A | 8/1992 | Darr |
| 5,229,104 A | 7/1993 | Sottery |
| 5,302,376 A | 4/1994 | Forestier |
| 5,346,694 A | 9/1994 | Juneja |
| 5,419,896 A | 5/1995 | Bimczok |
| 5,429,815 A | 7/1995 | Faryniarz |
| 5,496,538 A | 3/1996 | Zimmerman |
| 5,520,918 A | 5/1996 | Smith |
| 5,549,886 A | 8/1996 | Grollier |
| 5,549,888 A | 8/1996 | Venkateswaran |
| 5,567,427 A | 10/1996 | Papadakis |
| 5,607,921 A | 3/1997 | Bernard |
| 5,616,332 A | 4/1997 | Herstein |
| 5,629,004 A | 5/1997 | Candau |
| 5,654,341 A | 8/1997 | Struewing |
| 5,707,635 A | 1/1998 | Deckner |
| 5,718,906 A | 2/1998 | Martin |
| 5,718,908 A | 2/1998 | Fanelli |
| 5,736,128 A | 4/1998 | Chaudhuri |
| 5,759,558 A | 6/1998 | Epstein |
| 5,811,101 A | 9/1998 | Waltman |
| 5,824,666 A | 10/1998 | Deckner |
| 5,833,998 A | 11/1998 | Biedermann et al. |
| 5,871,764 A | 2/1999 | Diaz |
| 5,872,112 A | 2/1999 | Blank |
| 5,876,736 A | 3/1999 | Cohen |
| 5,939,082 A | 8/1999 | Oblong et al. |
| 5,961,999 A | 10/1999 | Bimczok |
| 5,968,528 A | 10/1999 | Deckner et al. |
| 5,972,359 A | 10/1999 | Sine et al. |
| 5,989,536 A | 11/1999 | Deckner |
| 5,993,832 A | 11/1999 | Lorant |
| 6,001,379 A | 12/1999 | Griat |
| 6,042,813 A | 3/2000 | Fowler |
| 6,045,779 A | 4/2000 | Mueller |
| 6,099,825 A | 8/2000 | Mcshane |
| 6,153,176 A | 11/2000 | Kaleta |
| 6,174,533 B1 | 1/2001 | SaNogueira, Jr. et al. |
| 6,217,887 B1 | 4/2001 | Beerse |
| 6,218,347 B1 | 4/2001 | Rau |
| 6,224,888 B1 | 5/2001 | Vatter et al. |
| 6,238,678 B1 | 5/2001 | Oblong et al. |
| 6,261,541 B1 | 7/2001 | Karpov |
| 6,281,203 B1 | 8/2001 | Touzan |
| 6,287,582 B1 | 9/2001 | Gott |
| 6,287,583 B1 | 9/2001 | Warren |
| 6,299,885 B1 | 10/2001 | Yamasaki |
| H0002013 H | 2/2002 | Boyd et al. |
| 6,387,918 B1 | 5/2002 | Yamanaka |
| 6,410,039 B1 | 6/2002 | Walker |
| 6,416,768 B1 | 7/2002 | Ravaux |
| 6,419,907 B1 | 7/2002 | Hocquaux |
| 6,432,415 B1 | 8/2002 | Osborne |
| 6,440,432 B1 | 8/2002 | Mukherjee |
| 6,440,437 B1 | 8/2002 | Krzysik et al. |
| 6,461,622 B2 | 10/2002 | Liu |
| 6,468,549 B1 | 10/2002 | Dupuis |
| 6,492,326 B1 | 12/2002 | Robinson |
| 6,524,598 B2 | 2/2003 | Sunkel |
| 6,585,984 B1 | 7/2003 | Scott |
| 6,589,514 B2 | 7/2003 | Jensen et al. |
| 6,632,444 B1 | 10/2003 | Zhou |
| 6,638,519 B1 | 10/2003 | Lorant |
| 6,682,750 B2 | 1/2004 | Loeffler |
| 6,696,049 B2 | 2/2004 | Vatter et al. |
| 6,706,259 B1 | 3/2004 | Gardner |
| 6,759,051 B2 | 7/2004 | Saint-leger |
| 6,831,107 B2 | 12/2004 | Dederen |
| 6,903,210 B2 | 6/2005 | Behrends |
| 6,906,106 B2 | 6/2005 | Chevalier |
| 6,932,976 B2 | 8/2005 | Brooks |
| 6,979,452 B2 | 12/2005 | Zhou |
| 6,986,895 B2 | 1/2006 | Suares |
| 7,018,660 B2 | 3/2006 | Murad |
| 7,176,191 B2 | 2/2007 | Dale |
| 7,179,771 B1 | 2/2007 | Charlton |
| 7,291,351 B2 | 11/2007 | Azik |
| 7,300,678 B2 | 11/2007 | Paufique |
| 7,332,152 B2 | 2/2008 | Sanzgiri |
| 7,378,083 B2 | 5/2008 | Stephens |
| 7,416,719 B2 | 8/2008 | Huerta |
| 7,455,849 B2 | 11/2008 | Utschig |
| 7,741,366 B2 | 6/2010 | Mackles |
| 7,799,356 B2 | 9/2010 | Raschke |
| 7,815,900 B1 | 10/2010 | Cannell et al. |
| 7,829,107 B2 | 11/2010 | Popp |
| 8,063,097 B2 | 11/2011 | Robinson |
| 8,106,184 B2 | 1/2012 | Sauve |
| 8,197,807 B2 | 6/2012 | Brenner |
| 8,293,279 B2 | 10/2012 | Schiffer |
| 8,293,784 B2 | 10/2012 | Rudolph |
| 8,329,758 B2 | 12/2012 | Ali |
| 8,343,902 B2 | 1/2013 | Walters |
| 8,383,086 B2 | 2/2013 | Brenner |
| 8,435,950 B2 | 5/2013 | Dal |
| 8,475,851 B2 | 7/2013 | Herrmann |
| 8,491,464 B2 | 7/2013 | Yokoi |
| 8,529,920 B2 | 9/2013 | Liu |
| 8,529,979 B2 | 9/2013 | Abril |
| 8,546,364 B2 | 10/2013 | Patel |
| 8,652,447 B2 | 2/2014 | Maesen |
| 8,828,410 B2 | 9/2014 | Sakuta |
| 8,883,215 B2 | 11/2014 | Beck |
| 8,895,034 B2 | 11/2014 | Bennett |
| 8,895,513 B2 | 11/2014 | Trudsoe |
| 8,911,774 B2 | 12/2014 | Giampapa |
| 8,933,217 B2 | 1/2015 | Rinsch |
| 8,968,755 B2 | 3/2015 | Schlessinger |
| 8,999,923 B2 | 4/2015 | Cao et al. |
| 9,034,833 B1 | 5/2015 | Chiou et al. |
| 9,068,148 B2 | 6/2015 | Tamareselvy |

(56) References Cited

U.S. PATENT DOCUMENTS

| | | |
|---|---|---|
| 9,084,734 B2 | 7/2015 | Collier |
| 9,186,304 B2 | 11/2015 | Claas |
| 9,271,912 B2 | 3/2016 | Fernandez Prieto et al. |
| 9,283,163 B2 | 3/2016 | Santhanam |
| 9,333,156 B2 | 5/2016 | Ito |
| 9,339,447 B2 | 5/2016 | Souzy |
| 9,364,414 B2 | 6/2016 | Domloge |
| 9,364,690 B2 | 6/2016 | Lorant |
| 9,381,144 B1 | 7/2016 | Hilt |
| 9,446,265 B2 | 9/2016 | Jansen et al. |
| 9,468,597 B1 | 10/2016 | Perry |
| 9,474,699 B2 | 10/2016 | Sun |
| 9,486,394 B2 | 11/2016 | Abram |
| 9,526,690 B2 | 12/2016 | Da Costa Pereira |
| 9,655,934 B2 | 5/2017 | Schiemann |
| 9,775,789 B2 | 10/2017 | Simmons |
| 9,795,544 B2 | 10/2017 | Lorant |
| 9,820,482 B2 | 11/2017 | Bingham |
| 9,833,398 B2 | 12/2017 | Hakozaki |
| 9,834,635 B2 | 12/2017 | Klug |
| 9,867,774 B1 | 1/2018 | Hakim |
| 9,895,300 B2 | 2/2018 | Schroeder |
| 9,949,902 B2 | 4/2018 | Mundschau |
| 10,124,030 B2 | 11/2018 | Goldsberry |
| 10,130,578 B2 | 11/2018 | Brillouet |
| 10,363,209 B2 | 7/2019 | Wu |
| 10,398,640 B2 | 9/2019 | Widgerow |
| 10,413,485 B2 | 9/2019 | Huang |
| 10,441,822 B2 | 10/2019 | Buckley |
| 10,449,126 B2 | 10/2019 | L'alloret |
| 10,512,595 B2 | 12/2019 | Jansen et al. |
| 10,660,838 B2 | 5/2020 | Hakozaki |
| 10,959,933 B1 | 3/2021 | Zhang et al. |
| 11,583,488 B2 | 2/2023 | Zhang et al. |
| 2001/0009671 A1 | 7/2001 | Helbiche |
| 2001/0024655 A1 | 9/2001 | Schneider |
| 2002/0022040 A1 | 2/2002 | Robinson et al. |
| 2002/0022052 A1 | 2/2002 | Dransfield |
| 2002/0042438 A1 | 4/2002 | Pelletier |
| 2002/0058704 A1 | 5/2002 | Malik |
| 2002/0168423 A1 | 11/2002 | Wurzburger |
| 2002/0193264 A1 | 12/2002 | Cannell et al. |
| 2003/0032617 A1 | 2/2003 | Harel et al. |
| 2003/0049212 A1 | 3/2003 | Robinson et al. |
| 2003/0091603 A1 | 5/2003 | Ohmori |
| 2003/0118620 A1 | 6/2003 | Zhang |
| 2003/0147968 A1 | 8/2003 | Farber |
| 2003/0158363 A1 | 8/2003 | Nakanishi |
| 2003/0165552 A1 | 9/2003 | Fox |
| 2003/0223982 A1 | 12/2003 | Schlotmann |
| 2004/0013784 A1 | 1/2004 | Costa |
| 2004/0028634 A1 | 2/2004 | Tanaka |
| 2004/0081672 A1 | 4/2004 | Gupta |
| 2004/0092482 A1 | 5/2004 | Gupta |
| 2004/0175347 A1 | 9/2004 | Bissett |
| 2004/0265268 A1 | 12/2004 | Jain |
| 2005/0008601 A1 | 1/2005 | Ariotto |
| 2005/0037036 A1 | 2/2005 | Nielsen |
| 2005/0100519 A1 | 5/2005 | Guth |
| 2005/0106194 A1 | 5/2005 | Schiltz |
| 2005/0170013 A1 | 8/2005 | Douglas |
| 2005/0176677 A1 | 8/2005 | Dal Farra et al. |
| 2005/0227327 A1 | 10/2005 | Brenner |
| 2005/0244348 A1 | 11/2005 | Lindemann |
| 2005/0267023 A1 | 12/2005 | Sinclair et al. |
| 2006/0018861 A1 | 1/2006 | Chen et al. |
| 2006/0034875 A1 | 2/2006 | Nakanishi et al. |
| 2006/0040851 A1 | 2/2006 | Ghosh |
| 2006/0127426 A1 | 6/2006 | Ross |
| 2006/0147508 A1 | 7/2006 | Gupta |
| 2006/0161121 A1 | 7/2006 | Klaveness |
| 2006/0165741 A1 | 7/2006 | Coffindaffer |
| 2006/0210499 A1 | 9/2006 | Hoeffkes |
| 2006/0229265 A1 | 10/2006 | Milburn et al. |
| 2006/0275237 A1 | 12/2006 | Bissett et al. |
| 2007/0027095 A1 | 2/2007 | Brenner |
| 2007/0196344 A1 | 8/2007 | Osborne et al. |
| 2007/0231288 A1 | 10/2007 | Arnaud et al. |
| 2007/0232508 A1 | 10/2007 | Oshimura |
| 2007/0232687 A1 | 10/2007 | Kato |
| 2007/0274932 A1 | 11/2007 | Suginaka et al. |
| 2008/0025932 A1 | 1/2008 | Bissett et al. |
| 2008/0057138 A1 | 3/2008 | Telford |
| 2008/0181956 A1 | 7/2008 | Ha |
| 2008/0206169 A1 | 8/2008 | Millikin |
| 2008/0206373 A1 | 8/2008 | Millikin |
| 2008/0247960 A1 | 10/2008 | Yuan |
| 2008/0287533 A1 | 11/2008 | Gupta |
| 2008/0299058 A1 | 12/2008 | Saito et al. |
| 2008/0312169 A1 | 12/2008 | Johnson et al. |
| 2008/0312181 A1 | 12/2008 | Harel et al. |
| 2008/0317795 A1 | 12/2008 | Traynor |
| 2009/0068219 A1 | 3/2009 | Elie |
| 2009/0196942 A1 | 8/2009 | Goyarts et al. |
| 2009/0197819 A1 | 8/2009 | Johnson et al. |
| 2009/0214628 A1 | 8/2009 | De |
| 2009/0215723 A1 | 8/2009 | Le |
| 2009/0232750 A1 | 9/2009 | St. Cyr |
| 2009/0317354 A1 | 12/2009 | Nishimura |
| 2010/0015072 A1 | 1/2010 | Polla et al. |
| 2010/0040608 A1 | 2/2010 | Wahren-Herlenius et al. |
| 2010/0092408 A1 | 4/2010 | Breyfogle et al. |
| 2010/0092412 A1 | 4/2010 | Gohier |
| 2010/0105638 A1 | 4/2010 | Den-braven |
| 2010/0183531 A1 | 7/2010 | Johncock |
| 2010/0189669 A1 | 7/2010 | Hakozaki |
| 2010/0203175 A1 | 8/2010 | Abdul-malak |
| 2010/0204323 A1 | 8/2010 | Theiler |
| 2010/0215726 A1 | 8/2010 | Roth |
| 2010/0239510 A1 | 9/2010 | Ha |
| 2010/0254919 A1 | 10/2010 | Bommarito |
| 2010/0272667 A1 | 10/2010 | Kyte, III et al. |
| 2010/0291190 A1 | 11/2010 | Giampapa |
| 2011/0097286 A1 | 4/2011 | Swanson |
| 2011/0101021 A1 | 5/2011 | Greer et al. |
| 2011/0117219 A1 | 5/2011 | Springer |
| 2011/0123467 A1 | 5/2011 | Roth |
| 2011/0152384 A1 | 6/2011 | Gunn |
| 2011/0158920 A1 | 6/2011 | Morley |
| 2011/0172160 A1 | 7/2011 | Cao |
| 2011/0229427 A1 | 9/2011 | Klug |
| 2011/0262025 A1 | 10/2011 | Jarrold et al. |
| 2011/0262560 A1 | 10/2011 | Dabe et al. |
| 2012/0003168 A1 | 1/2012 | Lyga et al. |
| 2012/0022013 A1 | 1/2012 | Sinclair et al. |
| 2012/0039967 A1 | 2/2012 | Lou |
| 2012/0093896 A1 | 4/2012 | Mongiat |
| 2012/0121534 A1 | 5/2012 | Thorel et al. |
| 2012/0128683 A1 | 5/2012 | Shantha |
| 2012/0148515 A1 | 6/2012 | Hakozaki et al. |
| 2012/0156146 A1 | 6/2012 | Hakozaki et al. |
| 2012/0172584 A1 | 7/2012 | Sauve et al. |
| 2012/0189684 A1 | 7/2012 | Buckley |
| 2012/0197016 A1 | 8/2012 | Laughlin, II et al. |
| 2012/0225050 A1 | 9/2012 | Knight et al. |
| 2013/0022557 A1 | 1/2013 | Swanson |
| 2013/0125317 A1 | 5/2013 | Rudolph |
| 2013/0156711 A1 | 6/2013 | Castro |
| 2013/0164234 A1 | 6/2013 | Gruber |
| 2013/0164265 A1 | 6/2013 | Flavin |
| 2013/0189211 A1 | 7/2013 | Marini |
| 2013/0295024 A1 | 11/2013 | Hammer |
| 2013/0319449 A1 | 12/2013 | Xavier et al. |
| 2014/0020701 A1 | 1/2014 | Galderisi |
| 2014/0065099 A1 | 3/2014 | Alvarez et al. |
| 2014/0090660 A1 | 4/2014 | Xavier et al. |
| 2014/0127332 A1 | 5/2014 | Bitler |
| 2014/0158148 A1 | 6/2014 | Mette |
| 2014/0170195 A1 | 6/2014 | Fassih et al. |
| 2014/0190507 A9 | 7/2014 | Xavier et al. |
| 2014/0328774 A1 | 11/2014 | Rout et al. |
| 2014/0328775 A1 | 11/2014 | Laughlin, II et al. |
| 2014/0336308 A1 | 11/2014 | Mateu et al. |
| 2014/0369943 A1 | 12/2014 | Pilz |

(56) References Cited

U.S. PATENT DOCUMENTS

| | | |
|---|---|---|
| 2015/0065476 A1 | 3/2015 | Aistrup |
| 2015/0118169 A1 | 4/2015 | Hakozaki et al. |
| 2015/0164941 A1 | 6/2015 | Munisekhar |
| 2015/0196464 A1 | 7/2015 | Jansen et al. |
| 2015/0209261 A1 | 7/2015 | Ross |
| 2015/0209272 A1 | 7/2015 | Weisman |
| 2015/0272860 A1 | 10/2015 | Mette |
| 2015/0272865 A1 | 10/2015 | Mette |
| 2015/0352022 A1 | 12/2015 | Laughlin, II et al. |
| 2015/0359723 A1 | 12/2015 | Kim |
| 2016/0000692 A1 | 1/2016 | Zamyatin et al. |
| 2016/0074643 A1 | 3/2016 | Mcildowie et al. |
| 2016/0077080 A1 | 3/2016 | Laughlin, II et al. |
| 2016/0089324 A1 | 3/2016 | Nijakowski |
| 2016/0095806 A1 | 4/2016 | Farber |
| 2016/0102179 A1 | 4/2016 | Wagner |
| 2016/0128944 A1 | 5/2016 | Chawrai |
| 2016/0151270 A1 | 6/2016 | Brooks |
| 2016/0199404 A1 | 7/2016 | Blotsky |
| 2016/0235646 A1 | 8/2016 | Shah et al. |
| 2016/0250134 A1 | 9/2016 | Castle |
| 2016/0250241 A1 | 9/2016 | Deren-Lewis et al. |
| 2016/0317418 A1 | 11/2016 | Hakazaki et al. |
| 2016/0317419 A1 | 11/2016 | Hakazaki et al. |
| 2016/0317420 A1 | 11/2016 | Hakazaki et al. |
| 2016/0374908 A1 | 12/2016 | Hakozaki et al. |
| 2016/0374918 A1 | 12/2016 | Dihora et al. |
| 2016/0374919 A1 | 12/2016 | Hakozaki et al. |
| 2017/0079408 A1 | 3/2017 | Lee |
| 2017/0121746 A1 | 5/2017 | Velasquez et al. |
| 2017/0165160 A1 | 6/2017 | Schulze Zur Wiesche |
| 2017/0172972 A1 | 6/2017 | Buge |
| 2017/0196795 A1 | 7/2017 | Hakozaki |
| 2017/0227011 A1 | 8/2017 | Zhou et al. |
| 2017/0266099 A1 | 9/2017 | Kroon |
| 2017/0333321 A1 | 11/2017 | Carnali |
| 2017/0360674 A1 | 12/2017 | Schulze Zur Wiesche |
| 2018/0015013 A1 | 1/2018 | Prendergast |
| 2018/0042840 A1 | 2/2018 | Almiñana Domènech |
| 2018/0104175 A1 | 4/2018 | Liu |
| 2018/0140518 A1 | 5/2018 | Deckner |
| 2018/0177703 A1 | 6/2018 | Perricone |
| 2018/0185283 A1 | 7/2018 | Buge |
| 2018/0271760 A1 | 9/2018 | Baca |
| 2018/0271881 A1 | 9/2018 | Buge |
| 2018/0280297 A1 | 10/2018 | Buge |
| 2018/0280298 A1 | 10/2018 | Buge |
| 2018/0311137 A1 | 11/2018 | Mckiernan |
| 2018/0344624 A1 | 12/2018 | Athwal |
| 2018/0369110 A1 | 12/2018 | Hakozaki |
| 2019/0021961 A1 | 1/2019 | Abels |
| 2019/0076811 A1 | 3/2019 | Lei |
| 2019/0125654 A1 | 5/2019 | Goldsberry |
| 2019/0240141 A1 | 8/2019 | Boland |
| 2019/0328631 A1 | 10/2019 | Lou |
| 2019/0380945 A1 | 12/2019 | Hakozaki |
| 2020/0002377 A1 | 1/2020 | Van Den Nest |
| 2020/0009123 A1 | 1/2020 | Hakozaki |
| 2020/0253851 A1 | 8/2020 | Hakozaki |
| 2021/0369588 A1 | 12/2021 | Zhang et al. |

FOREIGN PATENT DOCUMENTS

| | | |
|---|---|---|
| BR | 102013005446 A2 | 6/2015 |
| CA | 2517765 C | 7/2009 |
| CA | 2217032 C | 12/2009 |
| CA | 2767952 A1 | 1/2011 |
| CH | 711092 A2 | 11/2016 |
| CN | 1261780 A | 8/2000 |
| CN | 101182299 A | 5/2008 |
| CN | 100418507 C | 9/2008 |
| CN | 100457074 C | 2/2009 |
| CN | 101048375 B | 12/2012 |
| CN | 103070781 A | 5/2013 |
| CN | 103211717 A | 7/2013 |
| CN | 102670469 B | 10/2013 |
| CN | 103565721 A | 2/2014 |
| CN | 102871863 B | 4/2014 |
| CN | 102716511 B | 5/2014 |
| CN | 104274340 A | 1/2015 |
| CN | 104688617 A | 6/2015 |
| CN | 104688654 A | 6/2015 |
| CN | 104784084 A | 7/2015 |
| CN | 104812363 A | 7/2015 |
| CN | 104873436 A | 9/2015 |
| CN | 104983630 A | 10/2015 |
| CN | 105168677 A | 12/2015 |
| CN | 104168883 B | 5/2016 |
| CN | 105663022 A | 6/2016 |
| CN | 105769747 A | 7/2016 |
| CN | 103987372 B | 8/2016 |
| CN | 104095770 B | 8/2016 |
| CN | 105997548 A | 10/2016 |
| CN | 106214607 A | 12/2016 |
| CN | 106456476 A | 2/2017 |
| CN | 106729669 A | 5/2017 |
| CN | 106821849 A | 6/2017 |
| CN | 107137299 A | 9/2017 |
| CN | 107320355 A | 11/2017 |
| CN | 107427429 A | 12/2017 |
| CN | 108078889 A | 5/2018 |
| CN | 105640870 B | 12/2018 |
| CN | 108938445 A | 12/2018 |
| CN | 109010216 A | 12/2018 |
| CN | 109106806 A | 1/2019 |
| DE | 1949740 A1 | 7/1970 |
| DE | 2423637 A1 | 11/1975 |
| DE | 3029263 A1 | 3/1981 |
| DE | 10063658 A1 | 7/2002 |
| DE | 10063660 A1 | 7/2002 |
| DE | 10139582 A1 | 2/2003 |
| DE | 20220609 U1 | 12/2003 |
| DE | 60104036 T2 | 8/2004 |
| DE | 202004006865 U1 | 12/2004 |
| DE | 69828095 T2 | 1/2005 |
| DE | 102004008440 A1 | 9/2005 |
| DE | 102004035737 A1 | 3/2006 |
| DE | 60030917 T2 | 11/2006 |
| DE | 60032597 T2 | 2/2007 |
| DE | 19712980 B4 | 10/2008 |
| DE | 102007036499 A1 | 2/2009 |
| DE | 102007037432 A1 | 2/2009 |
| DE | 102008010921 A1 | 9/2009 |
| DE | 102010026465 A1 | 5/2011 |
| DE | 102010027180 A1 | 5/2011 |
| DE | 102011084904 A1 | 6/2012 |
| DE | 102011087883 A1 | 8/2012 |
| DE | 102011089357 A1 | 8/2012 |
| DE | 102011089612 A1 | 6/2013 |
| DE | 102013225182 A1 | 4/2014 |
| EP | 0134483 A2 | 3/1985 |
| EP | 0315541 A1 | 5/1989 |
| EP | 0350275 A3 | 6/1991 |
| EP | 0826366 A3 | 4/1998 |
| EP | 0995427 A3 | 5/2000 |
| EP | 1417954 A1 | 5/2004 |
| EP | 1459736 A1 | 9/2004 |
| EP | 1618867 A1 | 1/2006 |
| EP | 1815843 A2 | 8/2007 |
| EP | 1949887 A2 | 7/2008 |
| EP | 1779845 B1 | 10/2010 |
| EP | 1997537 A3 | 2/2012 |
| EP | 2020227 B1 | 8/2012 |
| EP | 2548549 A1 | 1/2013 |
| EP | 2033622 B1 | 3/2013 |
| EP | 1276513 B1 | 11/2013 |
| EP | 2057980 B1 | 4/2014 |
| EP | 1435771 B1 | 7/2015 |
| EP | 1609462 B1 | 7/2015 |
| EP | 3040065 A1 | 7/2016 |
| EP | 2793828 B1 | 8/2016 |
| EP | 3050900 A1 | 8/2016 |
| EP | 1776161 B1 | 10/2016 |
| EP | 1852102 B1 | 10/2016 |

(56) References Cited

FOREIGN PATENT DOCUMENTS

| | | |
|---|---|---|
| EP | 1904020 B1 | 10/2016 |
| EP | 2308456 B1 | 10/2016 |
| EP | 1786893 B2 | 11/2016 |
| EP | 1672037 B1 | 12/2016 |
| EP | 1813255 B1 | 11/2017 |
| EP | 1475080 B1 | 4/2018 |
| EP | 2263788 B1 | 7/2018 |
| EP | 3220883 B1 | 7/2018 |
| EP | 2696841 B1 | 10/2018 |
| EP | 3122325 B1 | 10/2018 |
| EP | 2677999 B1 | 12/2018 |
| ES | 2236040 T3 | 7/2005 |
| ES | 2222818 B1 | 3/2007 |
| ES | 2542529 T3 | 8/2015 |
| FR | 1464035 A | 7/1966 |
| FR | 2366841 B1 | 2/1980 |
| FR | 2555443 A1 | 5/1985 |
| FR | 2586693 A1 | 3/1987 |
| FR | 2832062 B1 | 2/2004 |
| FR | 2845596 A1 | 4/2004 |
| FR | 2845284 B1 | 12/2004 |
| FR | 2883170 A1 | 9/2006 |
| FR | 2883171 B1 | 5/2007 |
| FR | 2938188 A1 | 5/2010 |
| FR | 2975295 A1 | 11/2012 |
| FR | 2986429 A1 | 8/2013 |
| FR | 2989891 A1 | 11/2013 |
| GB | 2050829 B | 10/1983 |
| GB | 2270259 A | 3/1994 |
| GB | 2472379 A | 2/2011 |
| IN | 201641012427 A | 10/2017 |
| JP | 1041602 B2 | 9/1989 |
| JP | 2037206 B2 | 8/1990 |
| JP | 8092061 A | 4/1996 |
| JP | H11137212 A | 5/1999 |
| JP | 2954640 B2 | 9/1999 |
| JP | H11240827 A | 9/1999 |
| JP | 2000072616 A | 3/2000 |
| JP | 2000109421 A | 4/2000 |
| JP | 2000119155 A | 4/2000 |
| JP | 2000212061 A | 8/2000 |
| JP | 2001064150 A | 3/2001 |
| JP | 2001089316 A | 4/2001 |
| JP | 2001107078 A | 4/2001 |
| JP | 2001261570 A | 9/2001 |
| JP | 2002504504 A | 2/2002 |
| JP | 2002080335 A | 3/2002 |
| JP | 2002145723 A | 5/2002 |
| JP | 2003095842 A | 4/2003 |
| JP | 2003261437 A | 9/2003 |
| JP | 2004041010 A | 2/2004 |
| JP | 3519269 B2 | 4/2004 |
| JP | 2004123871 A | 4/2004 |
| JP | 2004137176 A | 5/2004 |
| JP | 2004161655 A | 6/2004 |
| JP | 2004210699 A | 7/2004 |
| JP | 2004210700 A | 7/2004 |
| JP | 2004217616 A | 8/2004 |
| JP | 3615759 B2 | 11/2004 |
| JP | 3643038 B2 | 2/2005 |
| JP | 2005035910 A | 2/2005 |
| JP | 2005041861 A | 2/2005 |
| JP | 2005110602 A | 4/2005 |
| JP | 2005139139 A | 6/2005 |
| JP | 2005162741 A | 6/2005 |
| JP | 2005232092 A | 9/2005 |
| JP | 2005281133 A | 10/2005 |
| JP | 3739100 B2 | 11/2005 |
| JP | 2005306751 A | 11/2005 |
| JP | 2005320260 A | 11/2005 |
| JP | 3747141 B2 | 12/2005 |
| JP | 2006028133 A | 2/2006 |
| JP | 2006083164 A | 3/2006 |
| JP | 2006143777 A | 6/2006 |
| JP | 3863675 B2 | 10/2006 |
| JP | 2007106697 A | 4/2007 |
| JP | 2007145716 A | 6/2007 |
| JP | 2007297559 A | 11/2007 |
| JP | 4072296 B2 | 1/2008 |
| JP | 2008143838 A | 6/2008 |
| JP | 2008231010 A | 10/2008 |
| JP | 2009024075 A | 2/2009 |
| JP | 4399332 B2 | 10/2009 |
| JP | 2009269919 A | 11/2009 |
| JP | 4589050 B2 | 9/2010 |
| JP | 2010202595 A | 9/2010 |
| JP | 2010533143 A | 10/2010 |
| JP | 4759912 B2 | 6/2011 |
| JP | 2011213676 A | 10/2011 |
| JP | 2011236176 A | 11/2011 |
| JP | 4931356 B2 | 2/2012 |
| JP | 2012097030 A | 5/2012 |
| JP | 5203623 B2 | 2/2013 |
| JP | 2013053147 A | 3/2013 |
| JP | 2013103892 A | 5/2013 |
| JP | 2013116884 A | 6/2013 |
| JP | 2013121955 A | 6/2013 |
| JP | 2013173730 A | 9/2013 |
| JP | 2013194030 A | 9/2013 |
| JP | 5427422 B2 | 12/2013 |
| JP | 2014001155 A | 1/2014 |
| JP | 2014051670 A | 3/2014 |
| JP | 2014062077 A | 4/2014 |
| JP | 2014080374 A | 5/2014 |
| JP | 2014111579 A | 6/2014 |
| JP | 2015500269 A | 1/2015 |
| JP | 2015147752 A | 8/2015 |
| JP | 2015178485 A | 10/2015 |
| JP | 5857104 B2 | 12/2015 |
| JP | 2016003199 A | 1/2016 |
| JP | 2016027037 A | 2/2016 |
| JP | 2016504377 A | 2/2016 |
| JP | 2016044171 A | 4/2016 |
| JP | 2016069306 A | 5/2016 |
| JP | 2016077836 A | 5/2016 |
| JP | 2016098199 A | 5/2016 |
| JP | 6005863 B2 | 9/2016 |
| JP | 2016183152 A | 10/2016 |
| JP | 2016532654 A | 10/2016 |
| JP | 6017953 B2 | 11/2016 |
| JP | 2016536305 A | 11/2016 |
| JP | 2017501225 A | 1/2017 |
| JP | 6183849 B2 | 8/2017 |
| JP | 6184825 B2 | 8/2017 |
| JP | 2017529368 A | 10/2017 |
| JP | 2017210408 A | 11/2017 |
| JP | 2018505130 A | 2/2018 |
| JP | 6362243 B2 | 7/2018 |
| JP | 2018168102 A | 11/2018 |
| KR | 20000024485 A | 5/2000 |
| KR | 20050006622 A | 1/2005 |
| KR | 20070014412 A | 2/2007 |
| KR | 20080082802 A | 9/2008 |
| KR | 20110007751 A | 1/2011 |
| KR | 20120087600 A | 8/2012 |
| KR | 20130088224 A | 8/2013 |
| KR | 20140001686 A | 1/2014 |
| KR | 20140055689 A | 5/2014 |
| KR | 1405615 B1 | 6/2014 |
| KR | 20140093349 A | 7/2014 |
| KR | 20140132243 A | 11/2014 |
| KR | 20150066811 A | 6/2015 |
| KR | 20160002093 A | 1/2016 |
| KR | 20160096548 A | 8/2016 |
| KR | 20160101371 A | 8/2016 |
| KR | 20160108971 A | 9/2016 |
| KR | 20160109869 A | 9/2016 |
| KR | 20170115956 A | 10/2017 |
| KR | 20180008071 A | 1/2018 |
| KR | 20180020664 A | 2/2018 |
| KR | 20180036232 A | 4/2018 |
| KR | 20180060701 A | 6/2018 |
| KR | 20190001136 A | 1/2019 |
| KR | 20190058950 A | 5/2019 |

(56) References Cited

FOREIGN PATENT DOCUMENTS

| | | |
|---|---|---|
| RU | 2400213 C2 | 9/2010 |
| TW | 201244748 A | 11/2012 |
| WO | 8806888 A1 | 9/1988 |
| WO | 9217159 A3 | 1/1993 |
| WO | 9307856 A1 | 4/1993 |
| WO | 9416710 A1 | 8/1994 |
| WO | 9524179 A1 | 9/1995 |
| WO | 9603970 A1 | 2/1996 |
| WO | 9720540 A1 | 6/1997 |
| WO | 9720542 A1 | 6/1997 |
| WO | 9823256 A1 | 6/1998 |
| WO | 9856343 A1 | 12/1998 |
| WO | 9920229 A1 | 4/1999 |
| WO | 9947141 A1 | 9/1999 |
| WO | 9943296 A3 | 11/1999 |
| WO | 9960995 A1 | 12/1999 |
| WO | 0024921 A1 | 5/2000 |
| WO | 0071093 A1 | 11/2000 |
| WO | 0170187 A1 | 9/2001 |
| WO | 0170188 A1 | 9/2001 |
| WO | 0181635 A1 | 11/2001 |
| WO | 0207685 A2 | 1/2002 |
| WO | 0207700 A2 | 1/2002 |
| WO | 0219984 A3 | 8/2002 |
| WO | 03022234 A1 | 3/2003 |
| WO | 2004024115 A1 | 3/2004 |
| WO | 2005004829 A1 | 1/2005 |
| WO | 2005004833 A1 | 1/2005 |
| WO | 2004100862 A3 | 2/2005 |
| WO | 2005034969 A1 | 4/2005 |
| WO | 2005044214 A1 | 5/2005 |
| WO | 2005049782 A1 | 6/2005 |
| WO | 2006040048 A1 | 4/2006 |
| WO | 2006081071 A1 | 8/2006 |
| WO | 2006120682 A2 | 11/2006 |
| WO | 2006127987 A2 | 11/2006 |
| WO | 2007002831 A2 | 1/2007 |
| WO | 2007101493 A1 | 9/2007 |
| WO | 200800534 A1 | 1/2008 |
| WO | 2008003779 A1 | 1/2008 |
| WO | 2008016298 A1 | 2/2008 |
| WO | 2007067735 A3 | 3/2008 |
| WO | 2008112964 A1 | 9/2008 |
| WO | 2009099419 A3 | 5/2010 |
| WO | 2009150408 A3 | 5/2010 |
| WO | 2010051852 A1 | 5/2010 |
| WO | 2010058272 A3 | 7/2010 |
| WO | 2011030123 A2 | 3/2011 |
| WO | 2011033858 A1 | 3/2011 |
| WO | 2011004175 A3 | 4/2011 |
| WO | 2011052224 A1 | 5/2011 |
| WO | 2011074143 A1 | 6/2011 |
| WO | 2012172199 A1 | 12/2012 |
| WO | 2013010032 A1 | 1/2013 |
| WO | 2013088371 A2 | 6/2013 |
| WO | 2011139492 A3 | 7/2013 |
| WO | 2013124820 A1 | 8/2013 |
| WO | 2011038022 A3 | 9/2013 |
| WO | 2013143776 A2 | 10/2013 |
| WO | 2014090513 A1 | 6/2014 |
| WO | 2014131514 A1 | 9/2014 |
| WO | 2014132060 A1 | 9/2014 |
| WO | 2014190128 A1 | 11/2014 |
| WO | 2015007567 A1 | 1/2015 |
| WO | 2015030702 A2 | 3/2015 |
| WO | 2015061512 A1 | 4/2015 |
| WO | 2015117757 A1 | 8/2015 |
| WO | 2015186114 A1 | 12/2015 |
| WO | 2016006821 A1 | 1/2016 |
| WO | 2016034519 A1 | 3/2016 |
| WO | 2015174772 A9 | 6/2016 |
| WO | 2016097965 A1 | 6/2016 |
| WO | 2016100634 A2 | 6/2016 |
| WO | 2016142551 A1 | 9/2016 |
| WO | 2016171464 A1 | 10/2016 |
| WO | 2016188691 A1 | 12/2016 |
| WO | 2017026405 A1 | 2/2017 |
| WO | 2017093788 A1 | 6/2017 |
| WO | 2017123512 A1 | 7/2017 |
| WO | 2017174756 A1 | 10/2017 |
| WO | 2017191382 A1 | 11/2017 |
| WO | 2017194268 A1 | 11/2017 |
| WO | 2017194292 A1 | 11/2017 |
| WO | 2017200979 A1 | 11/2017 |
| WO | 2018062922 A1 | 4/2018 |
| WO | 2018071640 A1 | 4/2018 |
| WO | 2018112586 A1 | 6/2018 |
| WO | 2018134714 A1 | 7/2018 |
| WO | 2018160509 A1 | 9/2018 |
| WO | 2018189194 A1 | 10/2018 |
| WO | 2018191296 A1 | 10/2018 |
| WO | 2018206962 A1 | 11/2018 |
| WO | 2019245011 A1 | 12/2019 |

OTHER PUBLICATIONS

Draelos et al., "Niacinamide-containing facial moisturizer improves skin barrier and benefits subjects with rosacea", Cutis, vol. 76, Aug. 2005, pp. 135-141.

Ebanks et al., "Mechanisms Regulating Skin Pigmentation: The Rise and Fall of Complexion Coloration", International Journal of Molecular Sciences, vol. 10, No. 9, Sep. 2009, pp. 4066-4087.

Eisele et al., The partial compositional characteristics of apple juice from 175 apple varieties, Journal of Food Composition and Analysis, vol. 18, No. 2-3, Mar. 1, 2005, pp. 213-221.

Ekman, et al., Overexpression of Psoriasin (S100A7) Contributes to Dysregulated Differentiation in Psoriasis, Acta Derm Venereol, Apr. 6, 2017, 97(4); 441-448.

Ferraz et al., "Kinetic α-Deuterium Isotope Effects for Enzymatic and Nonenzymatic Hydrolysis of Nicotinamide-β-Riboside", Archives of Biochemistry and Biophysics, vol. 191, No. 2, Dec. 1978, pp. 431-436.

Gillbro, et al., The use of gene arrays and corresponding connectivity mapping (Cmap) to identify novel anti-ageing ingredients, International Journal of Cosmetic Science, 2015, 37 (Suppl. 1), 9-14.

Glaser, et al., The Antimicrobial Protein Psoriasin (S100A7) Is Upregulated in Atopic Dermatitis and after Experimental Skin Barrier Disruption, Journal of Investigative Dermatology (2009), 129(3), 641-649; published online Aug. 28, 2008.

Hakozaki et al., "The effect of niacinamide on reducing cutaneous pigmentation and suppression of melanosome transfer", British Journal of Dermatology, vol. 147. No. 1, Jul. 1, 2002, pp. 20-31.

International Search Report and Written Opinion of the International Searching Authority, PCT/US2017/012786, dated Mar. 20, 2017, 13 pages.

International Search Report and Written Opinion of the International Searching Authority, PCT/US2019/040223, dated Oct. 25, 2019, 13 pages.

International Search Report and Written Opinion; Application No. PCT/US2018/038903; dated Aug. 31, 2018, 16 pages.

International Search Report and Written Opinion; Application No. PCT/US2019/037430; dated Sep. 30, 2019, 12 pages.

Khalifah et al., Kinetics of Nonenzymatic Glycation of Ribonuclease A Leading to Advanced Glycation End Products. Paradoxical Inhibition by Ribose Leads to Facile Isolation of Protein Intermediate for Rapid Post-Amadori Studies, Biochemistry, vol. 35, No. 15, Apr. 16, 1996, pp. 4645-4654.

Kimball et al., "Reduction in the appearance of facial hyperpigmentation after use of moisturizers with a combination of topical niacinamide and N-acetyl glucosamine: results of a randomized, double-blind, vehicle-controlled trial", British Journal of Dermatology 2010, vol. 162, No. 2, pp. 435-441.

Oppenheimer, Norman J., "NAD hydrolysis: Chemical and enzymaticmechanisms", Molecular and Cellular Biochemistry, vol. 138, 1994, pp. 245-251.

PCT/US2016/029943; ISR and Written Opinion, dated Jul. 1, 2016; 19 pages.

(56) References Cited

OTHER PUBLICATIONS

PCT/US2016/029945; ISR and Written Opinion, dated Jun. 27, 2016; 12 pages.
PCT/US2016/029951; ISR and Written Opinion, dated Aug. 23, 2016, 11 pages.
PCT/US2016/039924, ISR and Written Opinion, dated Aug. 26, 2016, 9 Pages.
PCT/US2016/039925, ISR and Written Opinion, dated Aug. 25, 2016, 9 Pages.
PCT/US2016/039926; ISR and Written Opinion, dated Aug. 22, 2016, 11 pages.
Seppic, "Sepimax (TM) Zen", Datasheet, 2015. 4 Pages.
Sinthupoom et al., Nicotinic acid and derivatives as multifunctional pharmacophores for medical applications, European Food Research and Technology, vol. 240, No. 1, Oct. 29, 2014, pp. 1-17.
Soma et al., "Moisturizing effects of topical nicotinamide on atopic dry skin", International Journal of Dermatology, vol. 44, No. 3, Mar. 2005, pp. 197-202.
Stillman, Alfred E., "Jaundice", Clinical Methods: The History, Physical, and Laboratory Examinations, Edition 3. 1990. Chapter 87, Available from: https://www.ncbi.nlm.nih.gov/books/NBK413/, pp. 448-456.
Trojahn et al., Characterizing Facial Skin Ageing in Humans : Disentangling Extrinsic from Intrinsic Biological Phenomena, BioMed Research International, vol. 2015, Article ID 318586, 9 pages, http://dx.doi.org/10.1155/2015/318586, Jan. 14, 2015.
Wohlrab, et al., "Niacinamide—Mechanisms of Action and Its Topical Use in Dermatology", Skin Pharmacology and Physiology 2014; vol. 27, pp. 311-315.
www.gnpd.com Record ID: 2347755, "Dark Circle Correcting Eye Swirl", Apr. 2014, 03 pages.
www.gnpd.com Record ID: 3497875, Tria Age-Defying Skincare Nourishing Eye Renewal Cream, Nov. 2015, 05 pages.
www.gnpd.com Record ID: 3708793, Anti-Wrinkle Face Cream, Neogen Agecure, Mar. 2016, 05 Pages.
Zackheim H.S., Treatment of Psoriasis With 6-Aminonicotinamide. Arch Dermatol. 1975;111(7):880-882. doi:10.1001/archderm.1975.01630190070007.
"Breakout Star Oil-Free Acne Moisturizer", ID#7460333, Tula Life, USA, Mintel GNPD [online], Mar. 2020, Retrieved from Internet: URL:https://portal.mintel.com.
U.S. Appl. No. 17/335,674, filed Jun. 1, 2021.
U.S. Appl. No. 17/335,718, filed Jun. 1, 2021, to first inventor Lu Zhang.
15807M2 PCT Search Report and Written Opinion for PCT/US2021/035139 dated Nov. 23, 2021.
Amico et al.,"Effects of Adalimumab, Etanercept and Ustekinumab on the Expression of Psoriasin (S100A7) in Psoriatic Skin", Journal of Dermatological Science, vol. 80, Issue 1, Oct. 2015, 7 pages.
15807 EP Search Report and Written Opinion for 21163764.0 dated Jan. 20, 2022, 4 pages.
All Office Actions; U.S. Appl. No. 17/688,126, filed Mar. 7, 2022.
Chen Jian, Principles of Food Chemistry, South China University of Technology Press, dated Feb. 28, 2015, pp. 145-146.
U.S. Appl. No. 17/688,126, filed Mar. 7, 2022, to first inventor Tomohiro (NMN) Hakozaki et al.
Mintel, Sym-Micro Essence, Retrieved from Internet: http://www.gnpd.com, May 2020, 9 pages.
Superdrug B. Confident Night Serum, online retrieved from "https://www.skincarisma.com/products/b/confident-night-serum/ingredient_list#info-section", No Known date, 14 Pages.
Final Office Action; U.S. Appl. No. 16/460,308 dated Nov. 27, 2020, 6 pages.
Final Office Action; U.S. Appl. No. 17/335,718 dated May 17, 2023, 15 pages.
Non-Final Office Action; U.S. Appl. No. 16/010,944 dated May 15, 2020, 7 pages.
Non-Final Office Action; U.S. Appl. No. 16/015,502 dated Oct. 28, 2019, 17 pages.
Non-Final Office Action; U.S. Appl. No. 16/460,308 dated May 28, 2020, 5 pages.
Non-Final Office Action; U.S. Appl. No. 16/460,308 dated Oct. 8, 2021, 7 pages.
Non-Final Office Action; U.S. Appl. No. 16/860,837 dated Feb. 4, 2021, 16 pages.
Non-Final Office Action; U.S. Appl. No. 17/335,718 dated Nov. 9, 2022, 15 pages.
Notice of Allowance; U.S. Appl. No. 15/402,332 dated Jun. 29, 2017, 7 pages.
Notice of Allowance; U.S. Appl. No. 15/402,332 dated Oct. 4, 2017, 5 pages.
Notice of Allowance; U.S. Appl. No. 16/010,944 dated Dec. 16, 2019, 9 pages.
Notice of Allowance; U.S. Appl. No. 16/010,944 dated May 31, 2019, 10 pages.
Notice of Allowance; U.S. Appl. No. 16/010,944 dated Nov. 17, 2020, 9 pages.
Notice of Allowance; U.S. Appl. No. 16/015,502 dated Apr. 14, 2020, 07 pages.
Notice of Allowance; U.S. Appl. No. 16/015,502 dated Mar. 11, 2020, 13 pages.
Notice of Allowance; U.S. Appl. No. 16/460,308 dated Feb. 15, 2023, 9 pages.
Notice of Allowance; U.S. Appl. No. 16/460,308 dated Feb. 22, 2022, 9 pages.
Notice of Allowance; U.S. Appl. No. 16/860,837 dated Jul. 8, 2021, 13 pages.

LOW pH SKIN CARE COMPOSITION AND METHODS OF USING THE SAME

FIELD

The present invention relates generally to lactic acid/sodium lactate buffer systems for low pH skin care compositions, which provide desirable skin sensory properties, good efficacy, and have a low potential for skin irritation. More specifically, the present invention relates to low pH skin care compositions comprising a lactic acid/lactate buffer system, a pH-stable polymer thickener, a low molecular weight silicone fluid, and a skin care active.

BACKGROUND

Skin is the first line of defense against environmental insults that would otherwise damage sensitive underlying tissue and organs. Additionally, skin plays a key role in a person's physical appearance. Not surprisingly, most people would like to have healthy, younger looking skin. And for some people, the tell-tale signs of skin aging such as thinning skin, wrinkles, and age spots are an undesirable reminder of the disappearance of youth. As a result, numerous skin care products are marketed to treat a variety of actual or perceived skin conditions, especially those associated with aging and dryness. Conventional skin care products typically include one or more ingredients for treating a skin condition of interest. For example, U.S. Pat. No. 5,968,528 discloses the use of niacinamide for treating signs of skin aging.

Typically, cosmetic compositions are formulated to have a slightly acidic to neutral pH (i.e., 5.0-7.0), which is believed to improve the stability of certain ingredients in the composition (e.g., niacinamide, salicylates, and neutralized thickeners). For example, U.S. Pat. No. 5,824,666 discloses the challenges of formulating low pH skin care compositions. However, formulating a skin care composition at low pH (e.g., 2.0-5.0) may also provide certain benefits such as bolstering the acid mantle of the skin, exfoliating the skin, improving skin texture, and/or providing flexibility in product formulation.

Accordingly, it would be desirable to provide a low pH skin care composition for improving the appearance of skin. It would also be desirable to provide a low pH skin care composition that is stable and has good feel properties.

SUMMARY

Disclosed herein is a low pH skin care composition, comprising about 0.1% to 10% of a vitamin $B_3$ compound; about 0.1% to 5% of a pH buffer comprising lactic acid and sodium lactate; about 0.1% to 5% of a polymer thickener comprising polyacrylate crosspolymer-6; and about 0.1% to 10% of a silicone fluid having a kinematic viscosity of 100 cSt or less at 25° C. The pH of the composition herein is between about 2.0 and about 5.0, and the composition exhibits a TRPV1 activation of less than about 10%. In some instances, the composition may also maintain a pH of less than 5.0 for at least 5 minutes after application to human skin.

DETAILED DESCRIPTION

Figure 1:
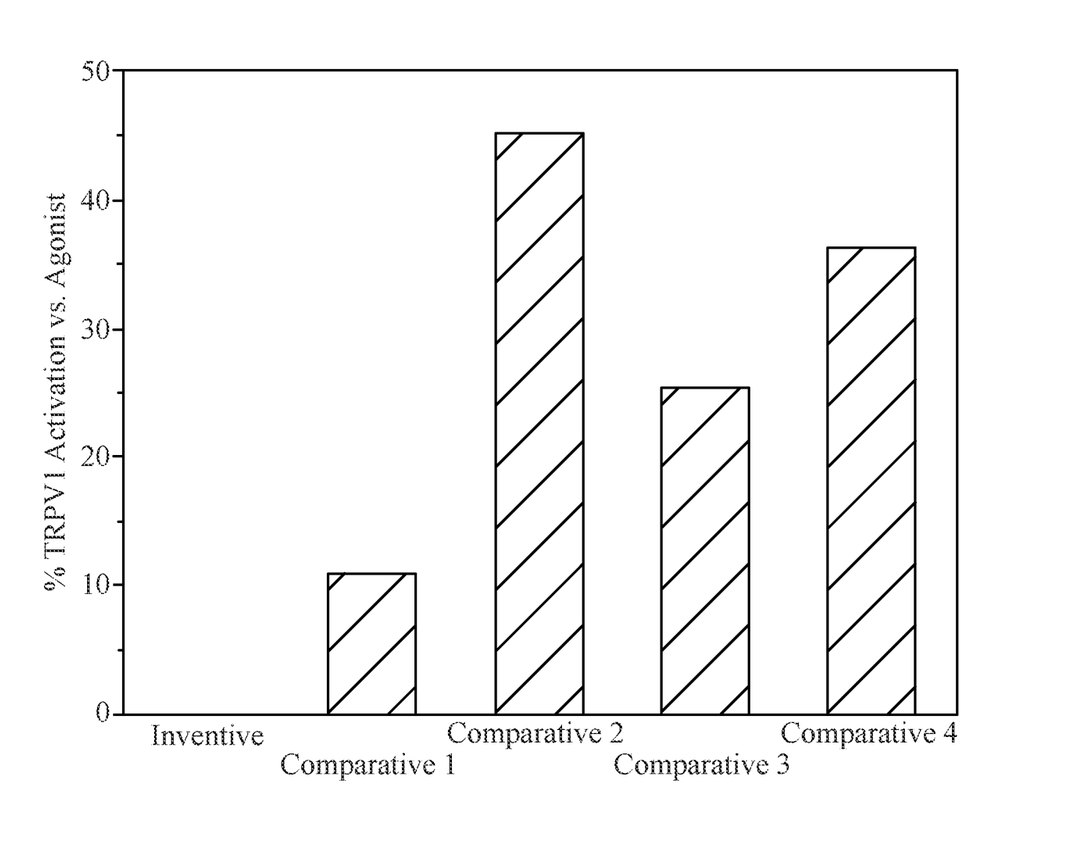
The FIGURE illustrates the results of the TRPV1 activation assay.

Conventional skin care products are typically formulated at neutral pH for a variety of reasons. For example, some conventional skin care products, if formulated at low pH, would have undesirable sensory properties (e.g., runny or sticky feeling) and/or exhibit instability (phase separation, cloudiness etc.). More recently, it has been found that certain skin care ingredients such as vitamin $B_3$ compounds and saccharides may be more efficacious at low pH. However, formulating low pH skin care products can still be challenging. For example, some thickeners that are tailored for use in low pH compositions, such as those described in WO20190245011, may impart an undesirable tackiness when applied to skin. In some instances, a low pH skin care product may be more likely to cause skin irritation in certain users (e.g., itching, burning, tingling, redness, discoloration, rash, bumps, or peeling). Surprisingly, it has now been discovered that a low pH skin care composition that includes niacinamide, a polymer thickener, a low molecular weight silicone oil, and a sodium lactate/lactic acid pH buffering system can provide an efficacious skin care product that does not irritate the skin and has better sensory properties than current low pH skin care products.

Reference within the specification to "embodiment(s)" or the like means that a particular material, feature, structure and/or characteristic described in connection with the embodiment is included in at least one embodiment, optionally a number of embodiments, but it does not mean that all embodiments incorporate the material, feature, structure, and/or characteristic described. Furthermore, materials, features, structures and/or characteristics may be combined in any suitable manner across different embodiments, and materials, features, structures and/or characteristics may be omitted or substituted from what is described. Thus, embodiments and aspects described herein may comprise or be combinable with elements or components of other embodiments and/or aspects despite not being expressly exemplified in combination, unless otherwise stated or an incompatibility is stated.

In all embodiments, all percentages are by weight of the cosmetic composition, unless specifically stated otherwise. All ratios are weight ratios, unless specifically stated otherwise. All ranges are inclusive and combinable. The number of significant digits conveys neither a limitation on the indicated amounts nor on the accuracy of the measurements. All numerical amounts are understood to be modified by the word "about" unless otherwise specifically indicated. Unless otherwise indicated, all measurements are understood to be made at approximately 25° C. and at ambient conditions, where "ambient conditions" means conditions under about 1 atmosphere of pressure and at about 50% relative humidity. All numeric ranges are inclusive of narrower ranges; delineated upper and lower range limits are interchangeable to create further ranges not explicitly delineated.

The compositions of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods. As used in the description and the appended claims, the singular forms "a," "an," and "the" are intended to include the plural forms as well, unless the context clearly indicates otherwise.

Definitions

"Apply" or "application", as used in reference to a composition, means to apply or spread the compositions of the present invention onto a human skin surface such as the epidermis.

"Cosmetic agent" means any substance, as well any component thereof, intended to be rubbed, poured, sprinkled, sprayed, introduced into, or otherwise applied to a mammalian body or any part thereof to provide a cosmetic effect. Cosmetic agents may include substances that are Generally Recognized as Safe (GRAS) by the US Food and Drug Administration, food additives, and materials used in non-cosmetic consumer products including over-the-counter medications.

"Effective amount" means an amount of a compound or composition sufficient to significantly induce a positive benefit to keratinous tissue over the course of a treatment period. The positive benefit may be a health, appearance, and/or feel benefit, including, independently or in combination, the benefits disclosed herein. In a specific example, an effective amount of a vitamin $B_3$ compound is an amount sufficient to improve the health and/or appearance of psoriatic skin during a treatment period. In some instances, an effective amount may be demonstrated using ex vivo and/or in vitro methods.

"Improve the appearance of" means providing a measurable, desirable change or benefit in skin appearance, which may be quantified, for example, by a decrease in redness, inflammation, and/or plaque scales.

"Low pH" means a pH of less than 5.0 (e.g., 1.5 to 4.9, 2.0 to 4.5, 2.5 to 4.0, or 3.5 to 4.0). A suitable method of determining the pH of a composition is described in more detail below.

"Neutral pH" means a pH of between 5.0 and 8.0.

"Safe and effective amount" means an effective amount of an ingredient that is low enough to avoid serious side effects (within the scope of sound medical judgment).

"Skin care" means regulating and/or improving a skin condition. Some nonlimiting examples include improving skin appearance and/or feel by providing a smoother, more even appearance and/or feel; increasing the thickness of one or more layers of the skin; improving the elasticity or resiliency of the skin; improving the firmness of the skin; and reducing the oily, shiny, and/or dull appearance of skin, improving the hydration status or moisturization of the skin, improving the appearance of fine lines and/or wrinkles, improving skin exfoliation or desquamation, plumping the skin, improving skin barrier properties, improve skin tone, reducing the appearance of redness or skin blotches, and/or improving the brightness, radiancy, or translucency of skin.

"Skin care active" means a compound or combination of compounds that, when applied to skin, provide an acute and/or chronic benefit to skin or a type of cell commonly found therein. Skin care actives may regulate and/or improve skin or its associated cells (e.g., improve skin elasticity, hydration, skin barrier function, and/or cell metabolism).

"Skin care composition" means a composition that includes a skin care active and regulates and/or improves skin condition.

"Treatment period," as used herein, means the length of time and/or frequency that a material or composition is applied to a target skin surface.

"Vehicle control" means a negative control that is identical to the test composition except that it does include the particular active(s) of interest (e.g., does not contain a vitamin $B_3$ compound).

Composition

The skin care composition herein is a low pH composition intended for topical application to human skin for improving skin appearance and/or function. In some instances, the present low pH composition may be used for non-therapeutic treatment of a variety of skin conditions. In some instances, the low pH composition may be particularly suitable for improving the appearance of hyperpigmented spots, uneven skin tone, and/or sallow looking skin.

The low pH skin care composition herein includes a safe and effective amount of a vitamin $B_3$ compound; a polymer thickener that can tolerate low pH environments; a low molecular weight silicone fluid; and a pH buffering system comprising lactic acid and sodium lactate. The composition may optionally include a silicone emulsifier as well as other ingredients commonly found in topical skin care compositions. It is believed, without being limited by theory, that this combination of ingredients provides an efficacious skin care composition that has good feel properties and is gentle on skin.

The cosmetic skin care composition herein can be made by mixing the ingredients with a dermatologically acceptable carrier using conventional methods known to those skilled in the art. The compositions may be provided in various product forms such as solutions, suspensions, lotions, creams, gels, toners, sticks, sprays, aerosols, ointments, cleansing liquid washes and solid bars, pastes, foams, mousses, shaving creams, wipes, strips, patches, electrically-powered patches, hydrogels, film-forming products, facial and skin masks (with and without insoluble sheet), and the like. The composition form may follow from the particular dermatologically acceptable carrier chosen. In some instances, the composition herein may be in the form of an essence. An essence is a form of topical skin care composition in a relatively concentrated formula that typically has a lower viscosity than conventional cream or lotion type skin care compositions. In some instances, an essence may be provided in the form of a low viscosity fluid that is marketed to specifically target a particular skin condition and/or be used in the first step of a skin care regimen. An essence product herein may have a dynamic viscosity of 1 centipoise (cP) to 15,000 cP at 25° C. (e.g., 50 cP to 10,000 cP or 100 cP to 7,500 cP, 200 cp to 5,000 cp, or 300 cp to 2,500 cp). The viscosity of the low pH compositions herein may be determined according to the Rheology Method provided in the Methods section below.

It has been found that at least some consumers desire a skin care essence that has a certain balance of transparency and opacity. If the essence is too transparent, it looks too much like water and consumers may be skeptical of the efficacy of the product. But if the essence is too opaque, consumers may think that product will not provide the light, clean feel that is expected from an essence. Thus, the low pH essence product herein has an opacity of between 45 and 85 (e.g., between 50 and 81, 55 and 77, or even between 60 and 73), according to the Opacity Test described in more detail below. In some instances, it may be desirable to limit the amount of hydrocarbon oils such as fatty alcohols and mineral oils present in the low pH essence, as these ingredients can significantly increase the opacity of the essence. Accordingly, it may be desirable to provide a low pH essence that is free or substantially free of hydrocarbon oils (e.g., less than 3%, 2%, 1%, 0.5%, or even 0%).

Vitamin $B_3$ Compound

The present composition includes a safe and effective amount of a vitamin $B_3$ compound for regulating a variety of skin condition, for example, as described in U.S. Pat. No. 5,939,082. The compositions herein may contain 0.1% to 10%, by weight, of the vitamin $B_3$ compound, based on the weight or volume of the composition (e.g., 0.5% to 5% or 1% to 4%).

As used herein, "vitamin $B_3$ compound" means a compound having the formula:

Where:
R is $CONH_2$ (i.e., niacinamide), COOH (i.e., nicotinic acid) or $CH_2OH$ (i.e., nicotinyl alcohol); derivatives thereof; and salts of any of the foregoing. Exemplary derivatives of vitamin $B_3$ compounds include nicotinic acid esters, including non-vasodilating esters of nicotinic acid (e.g., tocopheryl nicotinate, myristyl nicotinate) nicotinamide riboside, nicotinyl amino acids, nicotinyl alcohol esters of carboxylic acids, nicotinic acid N-oxide, and niacinamide N-oxide. In some instances, vitamin $B_3$ compounds such as niacinamide may have improved efficacy at lower pH, for example, as described in U.S. Publication No. 2020/0009123.

In some instances, it may be desirable for the ring nitrogen of the vitamin $B_3$ compound to be "uncomplexed" (e.g., chemically unbound and/or unhindered) in the composition and/or prior to application to a target skin surface. For example, the compositions herein may be free of or substantially free of (i.e., less than 3%, 2%, 1% or even less than 0.5%) a salt or complex of a vitamin $B_3$ compound. Exemplary approaches to minimizing or preventing the formation of undesirable salts and/or complexes include omission of materials that form substantially irreversible or other undesirable complexes with the vitamin $B_3$ compound in the composition, pH adjustment, ionic strength adjustment, the use of surfactants, and practicing formulation processes wherein the vitamin $B_3$ compound and materials which complex therewith are in different phases.

Low pH Acid Buffering System

A variety of acids are known for use in skin care compositions. For example, alpha hydroxy acids (e.g., citric acid, glycolic acid, malic acid, and lactic acid), beta hydroxy acids (e.g., salicylic acid and propanoic acid), and polyhydroxy acids (e.g., gluconic acid) are commonly used as exfoliants. However, some acids are stronger than others and/or some people may be more sensitive to certain concentrations of acids than others. Both of these factors can increase the risk of skin irritation caused by a low pH composition containing an acid. Lactic acid is one of the gentler alpha hydroxy acids when it comes to skin irritation, but it is still strong enough to provide the desired low pH in the present composition. In addition, lactic acid may provide skin benefits that are not provided by other alpha hydroxy acids (e.g., glycolic acid, citric acid or malic acid). For example, lactic acid may help improve the skin's natural moisture factor and/or stimulate collagen renewal to help improve the signs of aging skin. Thus, the compositions herein include lactic acid at an amount and concentration to provide the skin care composition herein with the desire low pH. In some instances, the low pH composition herein may include 0.5% to 5% lactic acid and/or gluconic acid (e.g., 0.75% to 4%, 1% to 3%, or 1.5% to 2.5%).

When providing a low pH composition for topical application to skin, it is important to include a buffering agent to help maintain the pH of the composition after it is applied to the skin. On average, human skin pH typically ranges from about 5.0 to 6.0. To maintain this pH, human skin has evolved a natural buffering system that resists changes to pH. Thus, when a low pH composition is applied to the skin, the skin's natural buffering system will try to adjust the pH of the composition to match the natural pH of the skin. Without the addition of the buffering agent, the low pH composition may not be able to provide the desired skin care benefit.

The low pH composition herein includes a sodium lactate and/or sodium gluconate buffering agent, depending on the acid(s) used in the composition for lowering the pH. The sodium lactate and/or sodium gluconate buffer may be present at any amount suitable for maintaining the pH of the present composition at the desired level upon application to the skin and for at least 1 minute thereafter (e.g., 5, 10, 15, 30, 60 or even 120 minutes or more after application) in order to provide enough time for the active ingredients in the composition to penetrate into the skin. In some instances, the sodium lactate may be present in the low pH composition at 0.25% to 4% (e.g., 0.5% to 3%, 0.75% to 2% or 1% to 1.75%). In some instances, the salt buffer may be present at a weight ratio acid to buffer of 1:10 to 10:1. It may be desirable to use the L-enantiomer form of the acid and/or salt buffer, since it is the form that occurs naturally in the body. In addition to acting as a buffering agent, sodium lactate may also act as a humectant to help moisturize the skin, which makes it a particularly suitable buffer. Of course, it is to be appreciated that the present composition may optionally include other pH buffers known for use in skin care compositions.

Thickeners

The composition includes a polymer thickener that can tolerate a low pH, electrolytic environment. That is, the thickener will not lose its ability to thicken or stabilize the composition at low pH in the presence of an acid-salt buffering system. Some conventional neutralized thickeners are known to degrade and/or lose the ability to suitably thicken a composition at lower pH and/or in the presence of an acid-salt buffer (e.g., sodium lactate). For example, sonic neutralized thickeners degrade in a low pH environment. On the other hand, fatty alcohol thickeners such as cetyl alcohols and stearyl alcohols are generally stable at low pH, but tend to impart an undesirable cloudiness or opacity to the composition when it is in the form of an essence, serum, or the like. it has also been found that certain anionic polymeric thickeners can provide suitable tolerance to low pH environments but cannot tolerate buffer systems due to combination of acid and salt. Thus, in some instances, the low pH composition described herein may be free or substantially free of neutralized thickeners, fatty alcohol thickeners, and anionic thickeners. The thickener may be present at 0.0001% to 25% (e.g., 0.001% to 20%, 0.01% to 10%, 0.5% to 7%, or 1% or 5%) by weight of the composition.

Other nonlimiting examples of thickeners or water structuring agents that may be used alone or in combination herein include natural or synthetic gums, polysaccharides, carboxylic acid polymers, polyacrylamide polymers, sulfonated polymers, and copolymers of these. Further examples include modified gums, celluloses, and superabsorbent polymers. The term "superabsorbent polymer" is understood to mean a polymer which is capable, in its dry state, of spontaneously absorbing at least 20 times its own weight of aqueous fluid, in particular of water and especially of distilled water. Suitable polysaccharides include alkyl hydroxyalkyl cellulose ethers, such as hydroxypropylmethylcellulose stearoxy ether. This material is sold under the tradename of SANGELOSE 60L and 90L from Daido Chemical Corp. Another suitable polysaccharide includes hydrophobically modified starch, such as Potato modified starch. This material is sold under the tradename of STRUCTURE SOLANACE by Nouryon. Another polymer includes crosslinked polymers, the monomers of which are at least partially composed of acryloyldimethyltaurate monomers, such as, for example sodium polyacryloyldimethyl taurate, sold under the tradename of ARISTOFLEX SILK, from Clariant.

It has now been found that certain anionic polymeric thickeners can provide suitable tolerance to low pH environments and the desired feel and opacity properties to the composition. Thus, a particularly suitable example of an anionic thickener is polyacrylate crosspolymer-6, which is commercially available as SEPIMAX ZEN from Seppic, France.

Low Molecular Weight Silicone Fluid.

In some instances, an anionic polymeric thickener may impart an undesirable tacky feel when the low pH composition is applied to a target portion of skin. It has been found that the addition of a low molecular weight silicone fluid can reduce or prevent this tacky feel. The molecular weight of a silicone fluid depends on the length of its silicone polymer chain(s), which is also directly proportional to the viscosity of the silicone fluid. Thus, the low molecular weight silicone fluids suitable for use in the present low pH composition have a kinematic viscosity of 100 cSt or less at 25° C. (e.g., 1 cSt to 90 cSt, 5 cSt to 50 cSt, or even 10 cSt to 30 cSt). Kinematic viscosity is a common method of classifying silicone fluids and can be obtained from the supplier of the material. A particularly suitable example of a low molecular weight silicone fluid is 5 cSt dimethicone fluid. As used herein, "dimethicone" means a polydimethylsiloxane compound having the formula:

Dermatologically Acceptable Carrier

The low pH compositions herein include a dermatologically acceptable carrier (which may be referred to as a "carrier"). The phrase "dermatologically acceptable carrier" means that the carrier is suitable for topical application to the keratinous tissue, has good aesthetic properties, is compatible with the actives in the composition, and will not cause any unreasonable safety or toxicity concerns. In one embodiment, the carrier is present at a level of from about 50% to about 99%, about 60% to about 98%, about 70% to about 98%, or, alternatively, from about 80% to about 95%, by weight of the composition.

The carrier can be in a wide variety of forms. In some instances, the solubility or dispersibility of the components (e.g., extracts, sunscreen active, additional components) may dictate the form and character of the carrier. Non-limiting examples include simple solutions (e.g., aqueous or anhydrous), dispersions, emulsions, and solid forms (e.g., gels, sticks, flowable solids, or amorphous materials). In some instances, the dermatologically acceptable carrier is in the form of an emulsion. The emulsion may have a continuous aqueous phase (e.g., an oil-in-water or water-in-oil-in-water emulsion) or a continuous oil phase (e.g., water-in-oil or oil-in-water-in-oil emulsion). The oil phase of the present invention may comprise silicone oils, non-silicone oils such as hydrocarbon oils, esters, ethers, and mixtures thereof. The aqueous phase typically comprises water and water-soluble ingredients (e.g., water-soluble moisturizing agents, conditioning agents, anti-microbials, humectants and/or other skin care actives). However, in some instances, the aqueous phase may comprise components other than water, including but not limited to water-soluble moisturizing agents, conditioning agents, anti-microbials, humectants and/or other water-soluble skin care actives. In some instances, the non-water component of the composition comprises a humectant such as glycerin and/or other polyol(s).

In some instances, the compositions herein are in the form of an oil-in-water ("O/W") emulsion that provides a sensorial feel that is light and non-greasy. Suitable O/W emulsions herein may include a continuous aqueous phase of more than 50% by weight of the composition, and the remainder being the dispersed oil phase. The aqueous phase may include 1% to 99% water, based on the weight of the aqueous phase, along with any water soluble and/or water miscible ingredients. In these instances, the dispersed oil phase will typically be present at less than 30% by weight of composition (e.g., 1% to 20%, 2% to 15%, 3% to 12%, 4% to 10%, or even 5% to 8%) to help avoid some of the undesirable feel effects of oily compositions. The oil phase may include one or more volatile and/or non-volatile oils (e.g., botanical oils, silicone oils, and/or hydrocarbon oils). Some nonlimiting examples of oils that may be suitable for use in the present compositions are disclosed in U.S. Pat. No. 9,446,265 and U.S. Publication No. 2015/0196464.

The carrier may contain one or more dermatologically acceptable, hydrophilic diluents. As used herein, "diluent" includes materials in which the vitamin $B_3$ compound can be dispersed, dissolved, or otherwise incorporated. Hydrophilic diluents include water, organic hydrophilic diluents such as lower monovalent alcohols (e.g., $C_1$-$C_4$) and low molecular weight glycols and polyols, including propylene glycol, polyethylene glycol (e.g., molecular weight of 200 to 600 g/mole), polypropylene glycol (e.g., molecular weight of 425 to 2025 g/mole), glycerol, butylene glycol, 1,2,4-butanediol, sorbitol esters, 1,2,6-hexanetriol, ethanol, isopropanol, sorbitol esters, butanediol, ether propanol, ethoxylated ethers, propoxylated ethers and combinations thereof.

Emulsifier

When the low pH composition herein is in the form of an emulsion (e.g., water emulsion), it may be desirable to include an emulsifier to stabilize the emulsion (i.e., prevent the emulsion from phase separating). The emulsifier may be present in the composition at 0.01% to 10% (e.g., 0.05% to 5% or 0.1% to 2%). The emulsifiers may be nonionic, anionic or cationic. In some instances, the emulsifier may be a silicone emulsifier. Some non-limiting examples of emulsifiers that may be suitable for use herein are disclosed in U.S. Pat. Nos. 3,755,560; 4,421,769; and McCutcheon's Detergents and Emulsifiers, North American Edition, pages 317-324 (1986).

Some other non-limiting examples of emulsifiers that may be suitable for use herein include ethers of polyglycols and of fatty alcohols, esters of polyglycols and of fatty acids, ethers of polyglycols and of fatty alcohols which are glycosylated, esters of polyglycols and of fatty acids which are glycosylated, ethers of C12-30 alcohols and of glycerol or of polyglycols, esters of C12-30 fatty acids and of glycerol or of polyglycerol, ethers of oxyalkylene-modified C12-30 alcohols and of glycerol or polyglycerol, ethers of C1-230 fatty alcohols comprising and of sucrose or of glucose, esters of sucrose and of C1230 fatty acids, esters of pentaerythritol and of C12-30 fatty acids, esters of sorbitol and/or of sorbitan and of C12 30 fatty acids, ethers of sorbitol and/or of sorbitan and of alkoxylated sorbitan, ethers of polyglycols and of cholesterol, esters of C12-30 fatty acids and of alkoxylated ethers of sorbitol and/or sorbitan, and combinations thereof. A particularly useful class of emulsifiers is polyethylene glycol ethers of lauryl alcohol such as laureth-1 through laureth-50 (e.g., laureth-4). Still other examples of emulsifiers include ethers of glycerol, polyglycerol, sucrose, glucose, or sorbitol; esters of glycerol, polyglycerol, sucrose, glucose, or sorbitol; and mixtures thereof. Other particularly useful classes of emulsifiers are the alkyl esters of sorbitol and sorbitol anhydrides such as polysorbate 20, polysorbate 21, and polysorbate 40.

Silicone emulsifiers may suitable for use herein. Linear or branched type silicone emulsifiers may also be used. Particularly useful silicone emulsifiers include polyether modified silicones such as KF-6011, KF-6012, KF-6013, KF-6015, KF-6015, KF-6017, KF-6043, KF-6028, and KF-6038 and polyglycerolated linear or branched siloxane emulsifiers such as KF-6100, KF-6104, and KF-6105; all from Shin-Etsu. A particular suitable emulsifier for use herein is PEG-11 methyl ether dimethicone, which is available from Shin-Etsu as KF-6011. Surprisingly, it was discovered that the PEG-11 methyl ether dimethicone emulsifier further reduced the tacky feel of the anionic polymer thickener, thereby improving the overall feel of the low pH composition. The emulsifier may be present at an amount of 0.1% to 10% (e.g., 1% to 5%, or 2%-4%).

Other Optional Ingredients

The present composition may optionally include one or more additional ingredients commonly used in cosmetic compositions (e.g., colorants, skin care actives, anti-inflammatory agents, sunscreen agents, emulsifiers, buffers, rheology modifiers, combinations of these and the like), provided that the additional ingredients do not undesirably alter the skin health or appearance benefits provided by the present compositions. The additional ingredients, when incorporated into the composition, should be suitable for use in contact with human skin tissue without undue toxicity, incompatibility, instability, allergic response, and the like. Some nonlimiting examples of additional actives include vitamins, minerals, peptides and peptide derivatives, sugar amines, sunscreens, oil control agents, particulates, flavonoid compounds, hair growth regulators, anti-oxidants and/or anti-oxidant precursors, preservatives, protease inhibitors, tyrosinase inhibitors, anti-inflammatory agents, moisturizing agents, exfoliating agents, skin lightening agents, sunless tanning agents, lubricants, anti-acne actives, anti-cellulite actives, chelating agents, anti-wrinkle actives, anti-atrophy actives, phytosterols and/or plant hormones, N-acyl amino acid compounds, antimicrobials, and antifungals. Other non-limiting examples of additional ingredients and/or skin care actives that may be suitable for use herein are described in U.S. Publication Nos. 2002/0022040; 2003/0049212; 2004/0175347; 2006/0275237; 2007/0196344; 2008/0181956; 2008/0206373; 2010/00092408; 2008/0206373; 2010/0239510; 2010/0189669; 2010/0272667; 2011/0262025; 2011/0097286; US2012/0197016; 2012/0128683; 2012/0148515; 2012/0156146; and 2013/0022557; and U.S. Pat. Nos. 5,939,082; 5,872,112; 6,492,326; 6,696,049; 6,524,598; 5,972,359; and 6,174,533.

When including optional ingredients in the compositions herein, it may be desirable to select ingredients that do not form complexes or otherwise undesirably interact with other ingredients in the composition at low pH, especially pH sensitive ingredients like niacinamide, salicylates and peptides. In some instances, it may be desirable to select skin care actives that function via different biological pathways so that the actives do not interfere with one another, which could reduce the efficacy of both agents. When present, the optional ingredients may be included at amounts of from 0.0001% to 50%; from 0.001% to 20%; or even from 0.01% to 10% (e.g., 50%, 40%, 30%, 20%, 10%, 5%, 4%, 3%, 2%, 1%, 0.5% or 0.1%), by weight of the composition.

Method of Use

The low-pH compositions herein are formulated for topical application to skin. The method of using the present low pH composition involves identifying a target portion of skin on a person in need of treatment or where treatment is desired (e.g., portions of skin exhibiting uneven skin tone, sallow looking skin, or skin that contains hyperpigmented spots) and applying an effective amount of the low-pH composition to the target portion of skin over the course of a treatment period. The effective amount of composition may vary based on the skin benefit desired by the user and/or the size of the treatment area. In some instances, the effective amount may range from 0.1 g to 5 g (e.g., 0.2 g to 4 g, 0.3 g to 2 g, or even 0.5 g to 1 g). The target portion of skin may be on a facial skin surface such as the forehead, perioral, chin, periorbital, nose, and/or cheek) or another part of the body (e.g., hands, arms, legs, back, chest). In some instances, a target portion of skin may be selected that does not currently exhibit signs of skin aging, such as hyperpigmented spots or uneven skin tone, but is an area of skin that commonly exhibits such features with age. In these instances, the low pH composition may be used to help prevent the occurrence of such undesirable skin features.

The composition may be applied locally to the target portion of skin in need of treatment and, if desired, to the surrounding skin at least once a day, twice a day, or on a more frequent daily basis, during a treatment period. When applied twice daily, the first and second applications are separated by at least 1 to 12 hours. Typically, the composition is applied in the morning and/or in the evening before bed. When used according to the methods herein, the present compositions may improve the appearance and/or function of skin, for example, by improving skin texture. Improvements in skin texture can be provided, for example, by decreasing pore size, reducing skin roughness, reducing the presence and/or size of wrinkles, combinations of these and the like.

The treatment period is ideally of sufficient time for the low-pH composition to improve the appearance and/or function of the target portion of skin. The treatment period typically lasts for at least 1 week (e.g., about 2 weeks, 4 weeks, 8 weeks, or even 12 weeks). In some instances, the treatment period may extend over multiple months (i.e., 3-12 months). In some instances, the composition is applied most days of the week (e.g., at least 4, 5 or 6 days a week), at least once a day or even twice a day during a treatment period of at least 2 weeks, 4 weeks, 8 weeks, or 12 weeks.

The step of applying the composition herein may be accomplished by localized application. In reference to application of the composition, the terms "localized", "local", or "locally" mean that the composition is delivered to the targeted area (e.g., a psoriatic plaque) while minimizing delivery to skin surfaces where treatment is not desired. The composition may be applied and lightly massaged into an area of skin. The form of the composition or the dermatologically acceptable carrier should be selected to facilitate localized application. While certain embodiments herein contemplate applying a composition locally to an area, it will be appreciated that compositions herein can be applied more generally or broadly to one or more skin surfaces. In certain embodiments, the compositions herein may be used as part of a multi-step beauty regimen, wherein the present composition may be applied before and/or after one or more other compositions.

Methods

Opacity Test Method

This method is used to determine the opacity of a product or material. Results are reported as a percentage, wherein higher the percentage the greater is the opacity of the sample. A spectrophotometer that can deliver tristimulus values CIE XYZ under CIE D65 lighting conditions across the visible spectrum (e.g., Spectrophotometer CM-3600A, Konica Minolta, Japan, or equivalent) is used for this method. The spectrophotometer is operated under conditions to deliver 1931 CIE defined tristimulus XYZ values with 2° observer and D65 illuminant. Portion samples are evaluated using a 10 mm path length in a plastic cell (such as CM-A131, Konica Minolta, Japan or equivalent), reflectance measurement, a 25.4 mm aperture opening at the specimen surface, specular component excluded. Two sets of tristimulus values are necessary to calculate opacity—one with the product's 10 mm sample cell in front of a white background and the other in front of a black background. Acceptable white backgrounds include the white portion of an opacity card (such as Opacity Card Form 2A, Leneta Company, Inc, Mahwah, NJ, USA, or equivalent) and acceptable black backgrounds are the black portion of an opacity card (such as Opacity Card Form 2A, Leneta Company, Inc, Mahwah, NJ, USA, or equivalent). Opacity is determined by calculating the quotient of the Y tristimulus value using the black background divided by the Y tristimulus value using the white background and multiplying by 100%. Opacity is reported to the nearest integer percentage.

Rheology Method

This method provides a way to measure the dynamic viscosity of a composition or material using a BROOKFIELD brand viscometer (e.g., model DV2T or equivalent) and a suitable spindle (e.g., RV4 or equivalent) according to the manufacturer's instructions. It is to be appreciated that the skilled artisan will be able to select the appropriate spindle in accordance with the manufacture's recommendation. After calibrating the viscometer, the spindle is immersed into a sufficient quantity of test sample (e.g., enough to immerse the spindle up to the immersion mark on the spindle shaft). Set the spindle rotation speed to 5 rpm, and then start the viscometer. Allow time for the indicated viscosity reading to stabilize (approximately 10-30 seconds). After the reading stabilizes, take 5 readings at 10 second intervals. Calculate the viscosity as the average of the 5 readings.

EXAMPLES

Example 1

Formulations

Table 1 provides examples of the low pH compositions described herein and a comparative example of a non-inventive composition (Example J). The compositions were prepared using conventional methods of making skin care compositions. Such methods typically involve mixing of the ingredients in one or more steps to a relatively uniform state, with or without heating, cooling, application of vacuum, and the like. Typically, emulsions are prepared by first mixing the aqueous phase materials separately from the fatty phase materials and then combining the two phases as appropriate to yield the desired continuous phase. The compositions are preferably prepared to optimize stability (physical stability, chemical stability, photostability) and/or delivery of the active materials. This optimization may include adjusting the pH (i.e., to less than 5), exclusion of materials that can complex with the active agent and thus negatively impact stability or delivery (e.g., exclusion of contaminating iron), use of approaches to prevent complex formation (e.g., appropriate dispersing agents or dual compartment packaging), use of appropriate photostability approaches (e.g., incorporation of sunscreen/sunblock, use of opaque packaging), etc.

The pH of the compositions tested in this example are measured with an ORION brand 525A pH meter (or equivalent) equipped with a flat surface electrode/probe (e.g., VWR Cat. 20 No. 89231-584). The probe of the pH meter is immersed directly into a neat sample of the composition. The compositions in the Examples have a pH of 3.8. It is believed, without being limited by theory, that a pH of 3.8 may provide the best balance between skin care active efficacy, sensory properties, and low irritation potential.

TABLE 1

| Component | A | B | C % | D | E | F |
|---|---|---|---|---|---|---|
| Water | qs | qs | qs | qs | qs | qs |
| Glycerin | 4.50 | 4.50 | 3 | 3 | 4.5 | 4.5 |
| Dimethicone 5 cSt | 4.00 | 4.00 | 3.00 | 4.00 | 4 | 1 |
| Dimethicone and dimethicone/vinyl dimethicone crosspolymer[1] | — | — | — | — | 4.5 | — |
| Niacinamide | 0.04 | 2 | 2 | 2 | 2 | 2 |
| Yeast Extract Hydrolyzed Yeast Protein[2] | — | 3 | — | — | — | — |
| Trifluoroacetyl Tripeptide-2[3] | — | 1 | — | — | — | — |
| Lactic acid | 2.00 | 1.62 | 1.62 | 1.62 | 1.62 | 1.62 |
| Sodium lactate | 1.80 | 0.78 | 0.78 | 0.78 | 0.78 | 0.78 |
| Polyacrylate crosspolymer-6[4] | 1.30 | 1.2 | 1.2 | 1 | 1.2 | 1.2 |
| Panthenol | .050 | 0.5 | 0.5 | 1 | 0.5 | 0.5 |
| Disodium EDTA | 1.00 | 0.1 | — | 0.1 | 0.1 | 0.1 |
| PEG-11 methylether dimethicone[5] | 0.10 | 0.10 | 0.10 | — | 0.10 | 0.1 |
| Laureth-4 | — | — | — | 0.2 | 0.2 | — |

TABLE 1-continued

| | | | | | | |
|---|---|---|---|---|---|---|
| Trehalose | 0.10 | 0.10 | 0.10 | 0.10 | 0.10 | 0.1 |
| Sodium Benzoate | 0.05 | 0.05 | 0.05 | 0.05 | 0.05 | 0.05 |
| Fragrance | 0.04 | 0.04 | — | 0.04 | — | — |
| pH | 3.8 | 3.8 | 3.8 | 3.8 | 3.8 | 3.8 |

| Component | H | I | J % | K | L |
|---|---|---|---|---|---|
| Water | qs | qs | qs | qs | qs |
| Glycerin | 4.5 | 3 | 4.5 | 4.5 | 4.5 |
| Dimethicone 5 cSt | 4 | 4 | — | — | — |
| Dimethicone 50 cSt | — | — | — | 4 | — |
| Dimethicone 100 cSt | — | — | — | — | 4 |
| Dimethicone and dimethicone/vinyl dimethicone crosspolymer | — | — | — | — | — |
| Niacinamide | 2 | 2 | 2 | 2 | 2 |
| Lactic acid | 1.62 | 1.62 | 1.62 | 1.62 | 1.62 |
| Sodium lactate | 0.78 | 0.78 | 0.78 | 0.78 | 0.78 |
| Polyacrylate crosspolymer-6 | 1.2 | 1.2 | 1.2 | 1.2 | 1.2 |
| Panthenol | 0.5 | 0.5 | 0.5 | 0.5 | 0.5 |
| Disodium EDTA | 0.1 | 0.1 | 0.1 | 0.1 | 0.1 |
| PEG-11 methylether dimethicone | — | 0.1 | — | 0.1 | 0.1 |
| Laureth-4 | — | — | — | — | — |
| Trehalose | 0.1 | 0.1 | 0.1 | 0.1 | 0.1 |
| Xylitol | — | 1.4 | — | — | — |
| Phenoxyethanol | — | 0.25 | — | — | — |
| Sodium Benzoate | 0.05 | 0.05 | 0.05 | 0.05 | 0.05 |
| Fragrance | — | — | — | — | — |
| pH | 3.8 | 3.8 | 3.8 | 3.8 | 3.8 |

[1] KSG-16 available from Shin-Etsu
[2] CHRONOGEN YST available from Ashland, Inc.
[3] PROGELINE available from Lucas Meyer Cosmetics
[4] SEPIMAX ZEN available from Seppic
[5] KF-6011 available from Shin-Etsu Example 2

Low pH Buffering System

This example demonstrates the ability of the lactic acid/sodium lactate low pH buffering system to maintain the pH of the composition below the average pH of normal human skin (i.e., less than 5.0). The test subjects were asked to wash their face with water prior to testing. A suitable amount (e.g., 1 g) of the test product (Example F from Table 1) was then applied to the face of the test subject. The pH of the target portion of skin was measured after the product dried (approximately 2-5 minutes after application) and then again 3 hours after application. The pH can be measured with a suitable pH meter with a flat probe by placing the probe against the skin of the test subject until a stable pH value is displayed by the pH meter. The pH probe should be dampened with DI water just prior to contacting the skin. The average pH from the test subjects is provided below in Table 2.

TABLE 2

| | Product pH | 2-5 minutes after application to skin | 3 hours after application to skin. |
|---|---|---|---|
| pH | 3.8 | 3.9 | 4.2 |

Example 3

Clinical Study

This example demonstrates the ability of the present low pH compositions to improve the appearance of skin. Texture Area Fraction was selected in the Example to show the desired skin appearance benefit provided by the low pH compositions. The method for determining Texture Area Fraction uses an objective image capture and analysis system to measure skin features that impact how skin texture is perceived (e.g., pore size, fine lines, and wrinkles). An improvement in Texture Area Fraction corresponds in an improvement in skin appearance.

A 9-week in vivo study was conducted using a randomized, vehicle controlled, balanced incomplete block, split face design including a 1-week washout period and an 8-week test period. Sixty subjects joined the treatment leg and 59 finished the study. The treatment regimen began with a 1-week washout period. Each morning and evening the subject was to wash her face with standard cleanser (Olay Deep cleansing facial Cleanser, available from The Procter & Gamble Company), gently dry with a towel, and apply a standard moisturizer (with 3% glycerin) to both sides of face. At baseline, each subject received two coded test formulations for twice daily application to either the left or right side of the face. Each morning and evening the subject was to wash her face with standard cleanser, gently dry with a towel, and apply 0.5 g of the appropriate test formulation on each side of the face with the fingers using gentle pressure in a circular motion. The test formulations used in this test were Example I from Table 1 and a vehicle control. The formula for the vehicle control is provided below in Table 3.

TABLE 3

| Control | |
|---|---|
| Component | % |
| Phase A | |
| water | qs |
| glycerin | 10.00 |
| Panthenol | 1.00 |
| disodium EDTA | 0.10 |
| Phase B | |
| Isopropyl Isostearate | 1.33 |
| Isohexadecane | 3.00 |
| cetearyl glucoside | 0.20 |
| cetyl alcohol | 0.32 |
| tocopherol acetate | 0.50 |
| PEG-100 stearate | 0.10 |
| stearyl alcohol | 0.48 |
| behenyl alcohol | 0.40 |
| ethyl paraben | 0.20 |
| propyl paraben | 0.10 |
| polymethylsilsesquioxane | 0.25 |
| Phase C | |
| polyacrylamide/C13-14 isoparaffin/laureth-7 | 2.00 |
| Phase D | |
| benzyl alcohol | 0.25 |
| dimethicone/dimethiconol | 2.00 |

Images of the facial treatment sites were captured at baseline, and after 2, 4 and 8 weeks of treatment and analyzed for changes to facial texture. Prior to image collection, the participants washed their face with a mild cleanser and then equilibrated for approximately 20 minutes prior to imaging Images were then collected of the right and left side of the participant's face using the Canfield OLÉ imaging system. The Canfield OLÉ imaging system (Canfield Scientific, Inc., Parsippany, New Jersey ,USA) is designed to capture reproducible facial images under controlled lighting and head positioning configurations in clinical research studies. The OLÉ imaging system incorporates a Canon EOS-6D DSLR which uses a 21-megapixel CMOS sensor with a maximum 5472×3648 resolution. The OLÉ imaging system saves both an Exif JPEG and Canon raw image file for each captured image.

Images of the test subjects are collected under different lighting modalities to enhance visualization of the skin features under investigation. An automated flash selection control and changeable filter control selects for the correct combination of lighting, lighting angles and filters that are optimized for the enhanced imaging of the facial topographical features (wrinkles, texture, etc.) or facial color feature (spots, tone, etc.). Reproducibility from time point to time point is facilitated with the aid of a live feed image of the subject superimposed on the baseline image. The subject is positioned such that all key landmarks on the face of the live image are exactly registered with those same landmarks of the baseline image. Each image contains a color chart with color chips of known values to assist in color management. Images captured with the OLÉ imaging system using the Canfield Capture software are saved directly to the data drive on the imaging system's computer.

In this Example, the region of interest (ROI) for texture measurements covered the test subject's upper and lower cheek, but did not extend into the undereye and central crow's feet areas. The upper limit of the mask followed along the subject's upper cheek bone. Specific differences in ROIs are due to variation in subject facial morphology. The degree of textured skin in the ROI were quantified objectively using image analysis algorithms based on an Optimus software platform. This analysis identified surface skin texture patterns that correlate to human perception of texture and quantified the total texture area detected in terms of pixels. Because the ROI varies in shape and size from subject to subject, the total texture area was normalized to the total ROI size to yield a Texture Area Fraction (TAF), i.e., the fractional ROI area occupied by facial texture in terms of pixels. The results of the tests are summarized in Table 4 below. As can be seen in Table 4, the low pH compositions significantly improved Texture Area Fraction compared to the vehicle and baseline values.

TABLE 4

| Texture Area Fraction (Example I) | | | | |
|---|---|---|---|---|
| Treatment Phase | ΔTAF vs. Vehicle | p-value | ΔTAF vs. Baseline | p-value |
| Week 2 | −0.098 | 0.0425 | −0.073 | 0.1983 |
| Week 4 | −0.249 | 0.0005 | −0.246 | <0.0001 |
| Week 8 | −0.215 | 0.0038 | −0.159 | 0.0181 |

Example 4

Reduced Tackiness

Nine test subjects were asked to apply the test products (blinded) on their forearm in CTCH room using control dosage. The test products used in this test were the compositions of Examples F, J, and H from Table 1. The test subjects were then asked to evaluate the tackiness at 2 minutes and at 6 minutes and give a score between 0 and 5, where zero is no tackiness and 5 is high tackiness. The results of the test are summarized in Table 5. A student T-test was used to determine statistical significance (threshold=0.05). Different letters (A, B, and C) indicate statistically significant difference between test legs, whereas same letter indicates no statistically significant difference. In other words, at 2 minutes, all three test legs demonstrated statistically significant differences in tackiness relative to one another, and at 6 minutes, Examples F and H exhibited statistically significant differences relative to Example J, but not to each other.

As can be seen in Table 5, Example F, which includes a low molecular weight silicone oil and a silicone emulsifier provided the lowest tacky feel after 2 minutes. Example H, which contains a low molecular weight silicone fluid but no silicone emulsifier had the second lowest tackiness. At 6 minutes, Examples F and H both provided statistically significant lower tackiness than Example J. Thus, the data suggest that adding the lower molecular weight silicone oil provides a reduction in tackiness and using a suitable silicone emulsifier can further reduce tackiness after application.

TABLE 5

|  | Example F | Example J | Example H |
|---|---|---|---|
| 2 mins tack | 1.2 A | 3.2 B | 2.0 C |
| 6 mins tack | 0.9 A | 3.2 B | 1.7 A |

*student T-test; threshold = 0.05

Example 5

Opacity

This example demonstrates the improved opacity properties of the present low pH composition relative to a composition in which the low molecular weight silicone oil is replaced with hydrocarbon oil. The compositions tested in this Example are provided in Table 6 below. The opacity of each composition was determined according to the opacity method described above. The results of the test are summarized in Table 7.

TABLE 6

| Component | Formula A | Formula B |
|---|---|---|
|  | % | |
| Water | q.s. | qs |
| Glycerin | 4.5 | 4.5 |
| Dimethicone 5 cSt | 4 | — |
| Dimethicone and dimethicone/vinyl dimethicone crosspolymer | — | — |
| Niacinamide | 2 | 2 |
| Lactic acid | 1.62 | 1.62 |
| Sodium lactate | 0.78 | 0.78 |
| Polyacrylate crosspolymer-6 | 1.2 | 1.2 |
| Panthenol | 0.5 | 0.5 |
| Disodium EDTA | 0.1 | 0.1 |
| PEG-11 methylether dimethicone | 0.1 | 0.1 |
| Laureth-4 | — | — |
| Trehalose | 0.1 | 0.1 |
| Xylitol | — | — |
| Phenoxyethanol | — | — |
| Sodium benzoate | 0.05 | 0.05 |
| Fragrance | — | — |
| Isopropyl lauroyl sarcosinate[1] | — | 4 |
| pH | 3.8 | 3.8 |

[1]ELDEW SL 205 available from Ajinomoto Omnichem

As can be seen in Table 7, Formula A (the composition that contains silicone oil) is able to provide the desired opacity of between 45 and 85, while the composition containing hydrocarbon oil (i.e., Formula B) did not.

TABLE 7

|  | Formula A | Formula B |
|---|---|---|
| Opacity | 83.54 | 87.3 |

Example 6

Low Irritation

This Example demonstrates the low irritation potential of the present low pH composition.

The low pH composition was tested in a clinical study, an in vitro cell-based assay and an in vivo human study to determine the relative irritation potential of the composition.

Clinical Study

As part of the clinical study described in Example 3 above, test subjects were asked to fill out a questionnaire that rated the level of irritancy associated with the test products that were applied to their skin. The questionnaire asked the test subjects to rate their test products for "Not Irritating the Skin." The questionnaire provided 7 possible answers: 1) Strongly Agree; 2) Agree; 3) Slightly Agree; 4) Don't Know; 5) Slightly Disagree; 6) Disagree; and 7) Strongly Disagree. The test composition used in this Example is Composition I from Table 1 and the vehicle control from Example 3. The results of the test at week 4 and week 8 are summarized below in Table 8. "Top 3" refers to the percent of test subjects who answered "Strongly Agree," "Agree," and "Slightly Agree."

TABLE 8

| Week | Treatment | Top 3 |
|---|---|---|
| 4 | Vehicle Control | 97% |
| 4 | Composition I | 98% |
| 8 | Vehicle Control | 98% |
| 8 | Composition I | 100% |

At week 4, 98% of test subjects agreed that the inventive composition did not irritate the skin versus 97% who agreed that the vehicle control did not irritate the skin. At week 8, 100% of the test subjects agreed that the test composition did not irritate the skin compared to 98% who agreed that the vehicle control did not irritate the skin. Thus, the results of this test suggest that that present low pH compositions can improve the appearance of skin without irritating the skin of the user.

In Vitro Study

The in vitro portion of this example examines the ability of a test composition to activate the well-known TRPV1 sensory receptor in commercially available HEK293 cells. TRP receptors (e.g., TRPA1, TRPV1 and TRPM8) are sensory receptors known for their involvement in communicating thermal sensations (i.e., hot and cold) to the central nervous system. TRPV1 is also believed to be involved in triggering skin sensorial irritations such as itching, burning, pain, tingling, stinging and inflammation. Specific human TRPV1 receptor expressing cell lines have previously been used to evaluate the ability of a material or composition to activate TRPV1, especially for evaluating the burning, tingling, taste sensation and/or pain relief effects of various consumer product formulations. In this example, HEK293 cells are pre-loaded with Fluo-4 AM, which is a calcium binding dye, and treated with control substances and test compositions in a high throughput manner using a FLIPR TETRA brand cellular screening system (available from Molecular Devices, LLC) or equivalent. Upon TRPV1 ion channel activation, calcium ions enter the cells and bind the Fluo-4 dye, producing a fluorescent signal, allowing quantification of the response. To reduce the impact of non-specific calcium mobilization unrelated to TRPV1 activation, formula responses are measured in the presence and absence of a specific TRPV1 inhibitor/antagonist compound. Positive signal of TRPV1 receptor activation by formula will disappear or be reduced in the presence of specific antagonists, thereby increasing the accuracy of data collection ascribed to formula-dependent TRPV1 activation.

TRPV1 Assay

To begin the assay, HEK293 cells are grown in DMEM media containing 10% FBS, high glucose, L-glutamine, phenol red, 100 ug/ml G418, and sodium pyruvate at 33° C. and 5% $CO_2$ for 4-5 days (80-90% confluent) (see, e.g., Sadofsky, L. R., et al. *Unique Responses are Observed in Transient Receptor Potential Ankyrin 1 and Vanilloid 1*

(*TRPA*1 and *TRPV*1) Co-Expressing Cells. Cells 2014, 3, 616-626). Cells at second passage are removed from the tissue culture vessel with PBS and the detached cells are spun in a centrifuge at low speed (800-1000 rpm) for 3 min to form a pellet. The PBS medium is removed and the cell pellet is resuspended in 4 mL growth medium. 50 µg of Fluo-4 AM calcium dye dissolved in 25 µL Pluronic F-127 is added and then the cells are incubated at room temperature for 1 hour with gentle shaking. The cells are washed once with 45 mL assay buffer (1× HBSS, 20 mM HEPES) by low speed centrifugation (800-1000 rpm) for 3 minutes and then re-suspended in 10 mL of the assay buffer. Dispense 100 µL aliquots (approximately 15×10$^4$ cells) in each well of a 96-well, black, flat-bottom plate. Let the plates sit at room temperature for 30 minutes and then record baseline fluorescence using the cellular screening system (e.g., FLIPR TETRA or equivalent) at $\lambda_{ex}$ 488 nm and $\lambda_{em}$ 514 nm. Capsaicin (350 nM) is used as the agonist control for each plate and ionomycin (2 uM) is used as the positive control.

Test samples are prepared as a 12× (10.8% formula) stock in assay buffer (w/v) and allowed to sit at room temperature for 1 hour. The test samples are then centrifuged at 14,000 rpm for 3 minutes. The aqueous phase is removed from the centrifuged sample and placed in a suitable tube and mix 1:1 in assay buffer to create a 6× stock. Prepare the TRPV1 antagonist composition by mixing the separated aqueous phase 1:1 with a 12× stock of the capsazepine (25 uM final concentration). Dilute the 6× samples 1:3 with assay buffer or 6× stock of the TRPV1 antagonist capsazepine (25 uM). Add 20 µL of the diluted composition to 96 well plates wells in triplicate for a final dilution of 0.3% formula.

The maximum fluorescence value in each well up to the time of the peak agonist control response is recorded (typically 40-50 seconds). Values of replicate wells are averaged and then converted to a percentage of the capsaicin agonist control response. Each test sample response is reported as the difference between the (mean test sample response)–(mean test sample response+antagonist). Responses that fall below zero are reported as "no response". The compositions tested in this study are provided below in Table 9. A summary of the results is illustrated in the Figure, which shows that the lactic acid/sodium lactate buffer system of the Inventive composition exhibited significantly less TRPV1 activation than the Comparative low pH compositions. Specifically, the lactate buffered composition exhibited less than 5% TRPV1 activation versus the agonist control.

TABLE 9

| Ingredients | Inventive 2.4% Lactate buffer | Comparative 1 3% Citate buffer | Comparative 2 4% citrate buffer | Comparative 3 L'Oreal Revitalift Derm Intensives 10% Pure Glycolic Acid Serum | Comparative 4 Neostrata Resurface Glycolic Renewal Smoothing Cream 10% AHA |
|---|---|---|---|---|---|
| Purified Water | 84.170 | 84.270 | 79.195 | Ingredient percentages not available | |
| D-Panthenol | 0.500 | 0.500 | 1.000 | | |
| Sodium Benzoate | 0.050 | 0.050 | 0.100 | | |
| Phenoxyethanol | 0.250 | 0.250 | 0.375 | | |
| Disodium EDTA | 0.100 | 0.100 | — | | |
| 1,2-Hexanediol and 1,2-Octanediol[1] | — | — | 0.800 | | |
| Niacinamide | 2.000 | 2.000 | 5.000 | | |
| Glycerin | 3.000 | 3.000 | 5.000 | | |
| Xylitol | 1.400 | 1.400 | 3.000 | | |
| Trehalose | 0.100 | 0.100 | — | | |
| 90% L-Lactic acid[2] | 1.800 | — | — | | |
| 60% Sodium L lactate[3] | 1.300 | — | — | | |
| Citric acid | — | 1.950 | 3.800 | | |
| Sodium Citrate | — | 1.050 | 0.200 | | |
| Polyacrylate crosspolymer-6[4] | 1.200 | 1.200 | 1.500 | | |
| Dimethicone 5cst | 4.000 | 4.000 | — | | |
| KF-6011P[5] | 0.100 | 0.100 | — | | |
| Perfume | 0.030 | 0.030 | 0.030 | | |
| TOTAL | 100.000 | 100.000 | 100.000 | | |
| pH | 3.81 | 3.85 | 3.51 | 3.95 | 3.61 |

[1]SYMDIOL 68 commercially available from Symrise
[2]PURAC HIPURE 90 commercially available from Corbion
[3]PURASAL S HQ-60 commercially available from Corbion
[4]SEPIMAX ZEN commercially available from Seppic
[5]KF-6011P commercially available from Shin-Etsu In Vivo Study The in vivo portion of this example illustrates the low irritation potential of the present compositions relative to comparative low pH formulations that use a different buffering system. This study was a single product, blinded test using female test subjects aged 25-54. The test subjects were asked to apply approximately 0.5 g (i.e., 1 pump) of the test composition to their entire face twice per day (morning and night). The compositions tested in this study are provided in Table 8 above. After 1 week of use, the test subjects were asked whether the test composition was irritating to the skin. The results of the in vivo study are summarized in Table 9 below. As can be seen in Table 9, the data suggest that the inventive example is less irritating to the skin than the comparative examples.

TABLE 10

|  | Inventive | Comparative 1 | Comparative 2 |
|---|---|---|---|
| Not Irritating Skin | 84.0% | 77% | 49.1% |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A low pH skin care composition, comprising:
   a) about 0.1% to 10% of niacinamide;
   b) about 0.1% to 5% of a pH buffer comprising lactic acid and sodium lactate;
   c) about 0.1% to 5% of a polymer thickener comprising polyacrylate crosspolymer-6; and
   d) about 0.1% to 20% of a silicone fluid having a kinematic viscosity of 100 cSt or less at 25° C.,
   e) wherein the composition has a pH of about 2.0 to about 5.0 and exhibits a TRPV1 activation of less than about 10% according to the TRPV1 assay.

2. The composition of claim 1, further comprising about 0.01% to about 1% of a silicone emulsifier.

3. The composition of claim 1, wherein the silicone fluid is dimethicone.

4. The composition of claim 1, further comprising a stable fatty alcohol thickener chosen from cetyl alcohols, stearyl alcohols, behenyl alcohols, or mixtures thereof.

5. The composition of claim 1, wherein the composition comprises at least one additional skin care active chosen from vitamins, minerals, peptides, sugar amines, sunscreens, oil control agents, flavonoid compounds, anti-oxidants, protease inhibitors, tyrosinase inhibitors, anti-inflammatory agents, moisturizing agents, exfoliating agents, skin lightening agents, anti-acne agents, anti-wrinkle agents, phytosterols, N-acyl amino acid compounds, antimicrobials, antifungals, or mixtures thereof.

6. The composition of claim 1, wherein the pH is about 2.5 to about 4.0.

7. The composition of claim 6, wherein the pH is about 3.5 to about 3.9.

8. The composition of claim 1, wherein the silicone fluid has a kinematic viscosity of 10 cSt or less.

9. The composition of claim 1, wherein the pH of the composition remains below 5.0 for at least 5 minutes after application to human skin.

10. A low pH skin care composition, comprising:
    a) about 0.1% to 10% of niacinamide;
    b) about 0.1% to 5% of a pH buffer comprising lactic acid and sodium lactate;
    c) about 0.1% to 5% of a polymer thickener comprising polyacrylate crosspolymer-6; and
    d) about 0.1% to 20% of a silicone fluid having a kinematic viscosity of 100 cSt or less at 25° C.,
    e) wherein the composition has a pH of about 2.0 to about 5.0 and exhibits a TRPV1 activation of less than about 10% according to the TRPV1 assey, and wherein the pH of the composition remains below 5.0 for at least 5 minutes after application to human skin.

11. The skin care composition of claim 10, wherein the pH of the composition remains below 5.0 for at least 10 minutes after application to human skin.

12. The skin care composition of claim 10, further comprising about 0.01% to about 1% of a silicone emulsifier.

13. The skin care composition of claim 10, wherein the silicone fluid is dimethicone.

14. The skin care composition of claim 10, further comprising a stable fatty alcohol thickener chosen from cetyl alcohols, stearyl alcohols, behenyl alcohols, or mixtures thereof.

15. The skin care composition of claim 10, wherein the composition comprises at least one additional skin care active chosen from vitamins, minerals, peptides, sugar amines, sunscreens, oil control agents, flavonoid compounds, anti-oxidants, protease inhibitors, tyrosinase inhibitors, anti-inflammatory agents, moisturizing agents, exfoliating agents, skin lightening agents, anti-acne agents, anti-wrinkle agents, phytosterols, N-acyl amino acid compounds, antimicrobials, antifungals, or mixtures thereof.

16. The skin care composition of claim 10, wherein the pH is about 2.5 to about 4.0.

17. The skin care composition of claim 15, wherein the pH remains below 4.0 for at least 5 minutes after application to human skin.

18. The skin care composition of claim 8, wherein the pH is about 3.5 to about 3.9.

19. The skin care composition of claim 17, wherein the pH remains below 3.9 for at least 5 minutes after application to human skin.

\* \* \* \* \*